US006228057B1

(12) United States Patent
Vasko

(10) Patent No.: US 6,228,057 B1
(45) Date of Patent: *May 8, 2001

(54) REMOTELY PROGRAMMABLE INFUSION SYSTEM

(75) Inventor: Robert S. Vasko, San Diego, CA (US)

(73) Assignee: I-Flow CORP, Lake Forest, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/251,021

(22) Filed: Feb. 16, 1999

Related U.S. Application Data

(63) Continuation of application No. 08/658,689, filed on Jun. 5, 1996, now Pat. No. 5,871,465, which is a continuation of application No. 08/344,973, filed on Nov. 25, 1994, now Pat. No. 5,573,506.

(51) Int. Cl.⁷ .................................................. A61M 1/00
(52) U.S. Cl. .......................... 604/151; 604/500; 128/904
(58) Field of Search .......................... 604/65, 67, 131, 604/151, 500, 506; 128/DIG. 12, DIG. 13, 904; 417/234; 222/52

(56) References Cited

U.S. PATENT DOCUMENTS

| 4,207,959 | 6/1980 | Youdin et al. . |
| 4,447,224 | 5/1984 | DeCant, Jr. et al. . |
| 4,676,776 | 6/1987 | Howson . |
| 4,692,147 | 9/1987 | Duggan . |
| 4,695,954 | 9/1987 | Rose . |
| 4,731,051 | 3/1988 | Fischell . |
| 4,782,511 | 11/1988 | Nemec et al. . |
| 4,838,887 | 6/1989 | Idriss . |
| 4,871,351 | 10/1989 | Feingold . |
| 4,941,172 | 7/1990 | Winebaum et al. . |
| 5,007,429 | 4/1991 | Treatch et al. . |
| 5,019,974 | 5/1991 | Beckers . |
| 5,078,683 | 1/1992 | Sancoff et al. . |
| 5,088,981 | 2/1992 | Howson et al. . |
| 5,100,380 | 3/1992 | Epstein et al. . |
| 5,165,874 | 11/1992 | Sancoff et al. . |
| 5,211,626 | 5/1993 | Frank et al. . |
| 5,226,086 | 7/1993 | Platt . |
| 5,228,449 | 7/1993 | Christ et al. . |
| 5,276,611 | 1/1994 | Ghiraldi . |
| 5,311,449 | 5/1994 | Adams . |
| 5,321,618 | 6/1994 | Gessman . |
| 5,335,313 | 8/1994 | Douglas . |
| 5,338,157 | * 8/1994 | Blomquist . |
| 5,369,699 | 11/1994 | Page et al. . |
| 5,394,445 | 2/1995 | Ball et al. . |

FOREIGN PATENT DOCUMENTS

PCT/US94/
07582    1/1995  (WO) .

* cited by examiner

Primary Examiner—Mark Bockelman
(74) Attorney, Agent, or Firm—Knobbe, Martens, Olson, Bear, LLP.

(57) ABSTRACT

A remotely programmable infusion system. The remotely programmable infusion system comprises a memory for storing a programmable protocol and a remote communication port for sending a voice signal to a remote touch-tone transceiver and for receiving a remote programming signal from the remote touch-tone transceiver. The remotely programmable infusion system also comprises a voice storage unit for storing the voice signal. The remotely programmable infusion system further comprises a processor, coupled to the remote communication port, to the voice storage unit, and to the memory, for accessing the voice signal from the voice storage unit and the programmable protocol from the memory, and for processing the programmable protocol in response to receiving the remote programming signal.

30 Claims, 14 Drawing Sheets

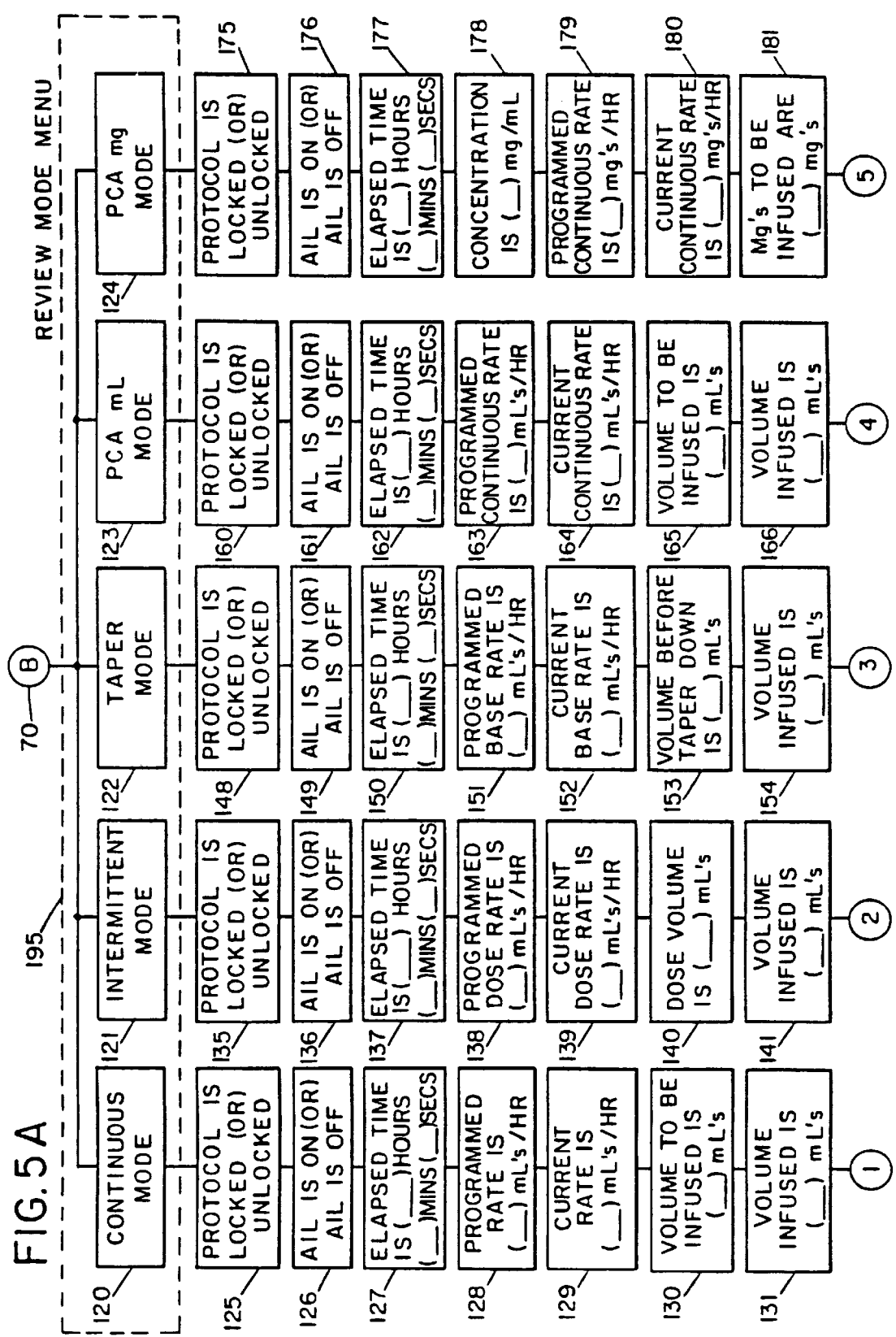

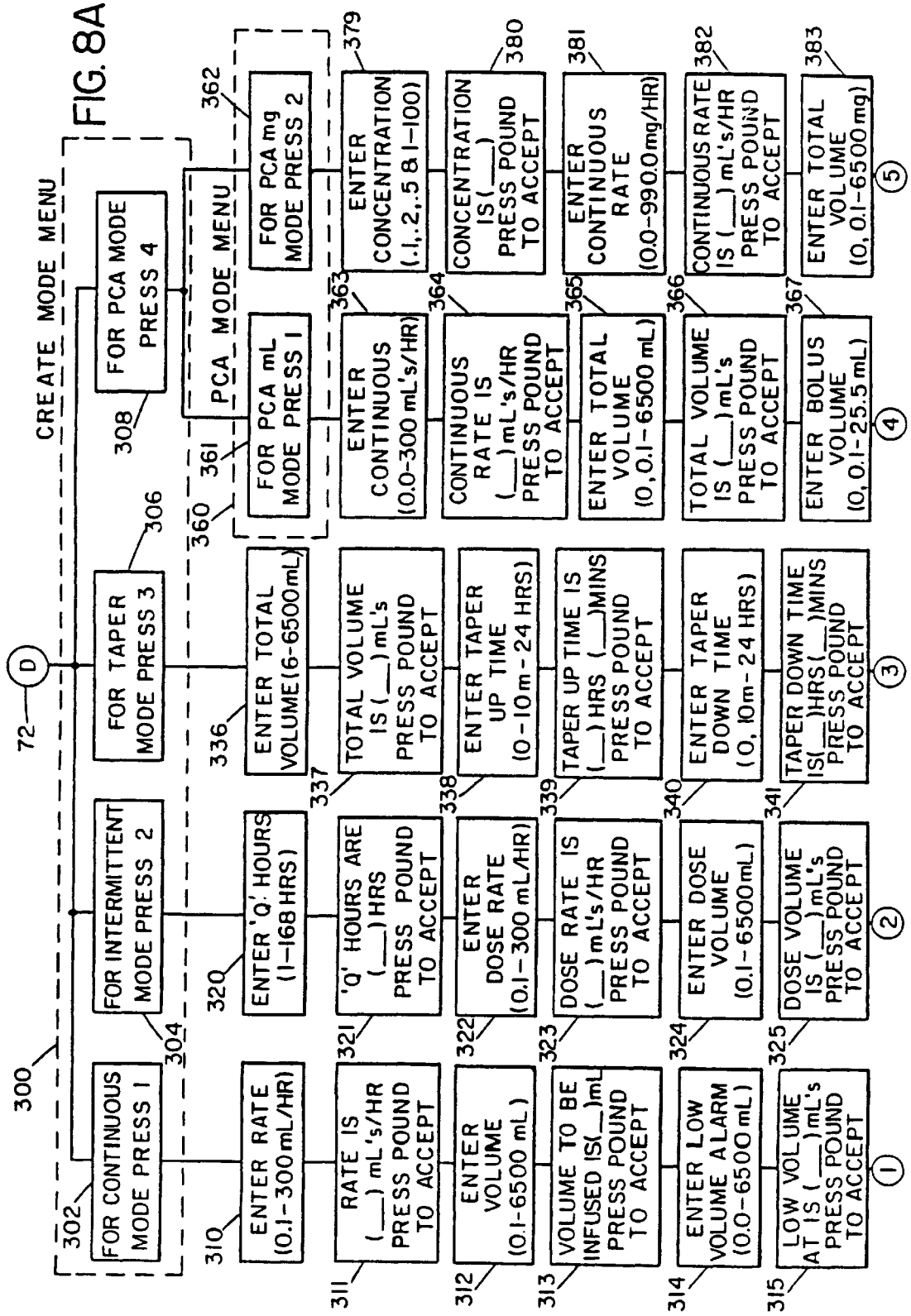

REMOTELY PROGRAMMABLE INFUSION SYSTEM

RELATED APPLICATIONS

This is a continuation application of prior application Ser. No. 08/658,689; filed Jun. 5, 1996 now U.S. Pat. No. 5,871,465, which is a continuation of application Ser. No. 08/344,973; filed Nov. 25, 1994, now issued as U.S. Pat. No. 5,573,506 on Nov. 12, 1996.

BACKGROUND OF THE INVENTION

1. Field of the Invention

The present invention relates to a remotely programmable infusion system for medical applications. More particularly, the present invention relates to an infusion system for delivering a variety of medicines and fluids that sends voice commands and queries to a remote touch-tone transceiver and that can be programmed by pressing keys on the keypad of the remote touch-tone transceiver in response to the commands and queries.

2. Description of the Related Art

Infusion devices are used in the medical field to administer and deliver medicines and other fluids to a patient. Today, due in part to rising health costs and the high cost of hospital rooms, and in part to the desire to provide comfort and convenience to patients, the medical industry has promoted in-home care for patients suffering from various maladies. Particularly, many patients require delivery and administration of medicines or other IV fluids on a regular basis. Delivery and administration is accomplished via a variety of infusion devices, such IV pumps and gravity pumps and other types of IV administration. By supplying patients with infusion devices that are lightweight and easy to use, the patients can receive their medicinal needs at home, i.e., without having to be at a hospital and without direct assistance by a care provider, such as a nurse.

Nevertheless, the operating parameters of infusion devices must frequently be changed, due to variations in the patient's needs. Therapy changes may also require that entire protocols be programmed. In early versions of home infusion devices, the physical presence of a care provider at the infusion device was required to reprogram the device's protocol. Such reprogramming was costly and time-consuming, thereby severely limiting the efficiency and convenience of infusion devices.

Since the introduction of these early home infusion devices, the medical industry has made advances in the techniques by which a home infusion device can be monitored and reprogrammed. For example, one system employs a patient activated switch on a diagnostic apparatus that causes automatic dialing of a telephone number corresponding to a care provider remote from the diagnostic apparatus. This enables the patient to communicate with the care provider through a speaker and microphone on the diagnostic apparatus, permitting interactive communication with the care provider regarding the routines to be performed by the diagnostic apparatus. This system, however, merely provides the capability for the care provider to monitor the infusion device, but does not offer the capacity to remotely reprogram the infusion device.

Another remote monitoring system employs a user interface for programming blood pressure testing protocol into, and downloading blood pressure data from, ambulatory blood pressure monitoring units. The user interface is connected to a central processing computer via a telephone line. Control units located at the blood pressure testing site transfer blood pressure data to the central computer, which generates comprehensive medical reports for specific patients, but which cannot transmit reprogramming signals back to the control unit.

Other systems employ remote computers for monitoring and reprogramming the protocol of the infusion device. In one such system, the infusion device has a delivery unit for delivering the medicinal solution and a removable logic unit for controlling operation of the delivery unit. The logic unit is either attached to or separate from the delivery unit, and the latter can be worn by the patient. The logic unit is connected to a programming computer via a telephone line. The computer can be used to program the logic unit with a logic configuration suitable for operating the delivery unit in accordance with the intended delivery requirements. Thus, while such systems provide for remote reprogramming of the protocol, they require a remotely located computer to accomplish reprogramming.

The previous conventional systems have a variety of drawbacks. Most importantly, they do not provide simple, interactive reprogramming by a care provider without the need for a remote reprogramming computer. The ability to have the care provider access the remotely located infusion device on a standard telephone and reprogram the infusion device via the keys on the telephone keypad is a significant advance over conventional reprogramming techniques. This is because touch-tone reprogramming is less costly, quicker, and much more convenient for both the care provider and the patient, making infusion devices easier to use and more versatile.

Conventional home infusion systems also do not have the capacity to send recorded voice signals to the remote care provider instructing and asking the care provider about reprogramming the infusion device. By using recorded voice commands and queries stored in the infusion system that direct the care provider in reprogramming the infusion device, the process of reprogramming is made simpler and more efficient, with little chance of making programming errors.

Therefore, a need exists for an infusion device that can be remotely programmed via a transceiver without the need for a remote programming computer and that sends recorded voice signals from the infusion device to a care provider.

SUMMARY OF THE INVENTION

Accordingly, the present invention is directed to a remotely programmable infusion system and a method for remotely programming an infusion system via a remote transceiver that substantially obviates one or more of the problems due to limitations and disadvantages of the related art.

Additional features and advantages of the invention will be set forth in the description that follows and in part will be apparent from the description, or may be learned by practice of the invention. The objectives and other advantages of the invention will be realized and attained by the apparatus and method particularly pointed out in the written description and claims of this application, as well as the appended drawings.

To achieve these and other advantages, and in accordance with the purpose of the invention as embodied and broadly described herein, the present invention defines a remotely programmable infusion system having a programmable protocol, the infusion system being remotely programmable by a remote touch-tone transceiver. The remotely programmable infusion system comprises a memory for storing a programmable protocol and a remote communication port for sending a voice signal to the remote touch-tone transceiver and for receiving a remote programming signal from the remote touch-tone transceiver. The remotely programmable infusion system also comprises a voice storage unit for storing the voice signal and a processor, coupled to the remote communication port and to the voice storage unit and to the memory, for accessing the voice signal from the voice storage unit and the programmable protocol from the memory, and for processing the programmable protocol in response to receiving the remote programming signal.

In another aspect, the present invention defines a method for remotely programming an infusion system. The infusion system has a voice storage unit for storing a voice signal and has a programmable protocol and is remotely programmable by a remote touch-tone transceiver. The method comprises several steps: establishing a connection between the infusion system and the remote touch-tone transceiver; accessing the voice signal from the voice storage unit in response to establishing the connection; sending the voice signal to the remote touch-tone transceiver; receiving a remote programming signal from the remote touch-tone transceiver; and processing the programmable protocol in response to receiving the remote programming signal.

In a further aspect, the present invention comprises a remotely programmable infusion system having a programmable protocol stored in a protocol memory, the remotely programmable infusion system being programmable by a remote touch-tone transceiver. The infusion system comprises an infusion pump for delivering fluids to a patient. The infusion pump has an infusion data port. The infusion system also comprises a homebase unit, coupled to the infusion communication port on the infusion pump via a homebase data port, for processing the programmable protocol. The homebase unit comprises a voice storage unit for storing a voice signal and a remote communication port for sending the voice signal to the remote touch-tone transceiver and for receiving a dual-tone multi-frequency (DTMF) signal from the remote touch-tone transceiver. The homebase unit further comprises a processor, coupled to the remote communication port, to the voice storage unit, and to the protocol memory, for accessing the voice signal from the voice storage unit, for accessing the programmable protocol from the protocol memory, and for processing the programmable protocol to obtain a processed programmable protocol in response to the DTMF signal. The processed programmable protocol is relayed from the processor to the infusion pump via the homebase data port and the infusion data port.

It is to be understood that both the foregoing general description and the following detailed description are exemplary and explanatory only and are not restrictive of the invention, as claimed.

The accompanying drawings are included to provide a further understanding of the invention and are incorporated in and constitute a part of this specification, to illustrate the embodiments of the invention, and, together with the description, to explain the principles of the invention.

BRIEF DESCRIPTION OF THE DRAWINGS

FIGS. 5A and 5B represent a flow diagram illustrating a review mode menu in accordance with an example of the present invention.

FIGS. 8A, 8B, and 8C represent a flow diagram illustrating a programming mode menu in accordance with an example of the present invention.

DESCRIPTION OF THE PREFERRED EMBODIMENT

Reference will now be made in detail to the present preferred embodiment of the invention, an example of which is illustrated in the accompanying drawings. Wherever possible, the same reference numbers will be used throughout the drawings to refer to the same or like parts.

In accordance with the present invention, a remotely programmable infusion system is provided that allows remote programming of the infusion system from a remotely located transceiver, such as a push-button telephone. The remotely programmable infusion system includes a memory and a voice storage unit. The infusion system also includes a remote communication port, as well as a processor that is coupled to the remote communication port, the voice storage unit, and the memory. It should be understood herein that the terms "programming," "programmable," and "processing" are generalized terms that refer to a host of operations, functions, and data manipulation. Those terms, therefore, are not to limited herein to editing and deleting data, parameters, protocol, and codes. For example, programming and processing, as used herein, may encompass editing, changing, erasing, entering, re-entering, viewing, reviewing, locking, and inserting functions.

Figure 1:
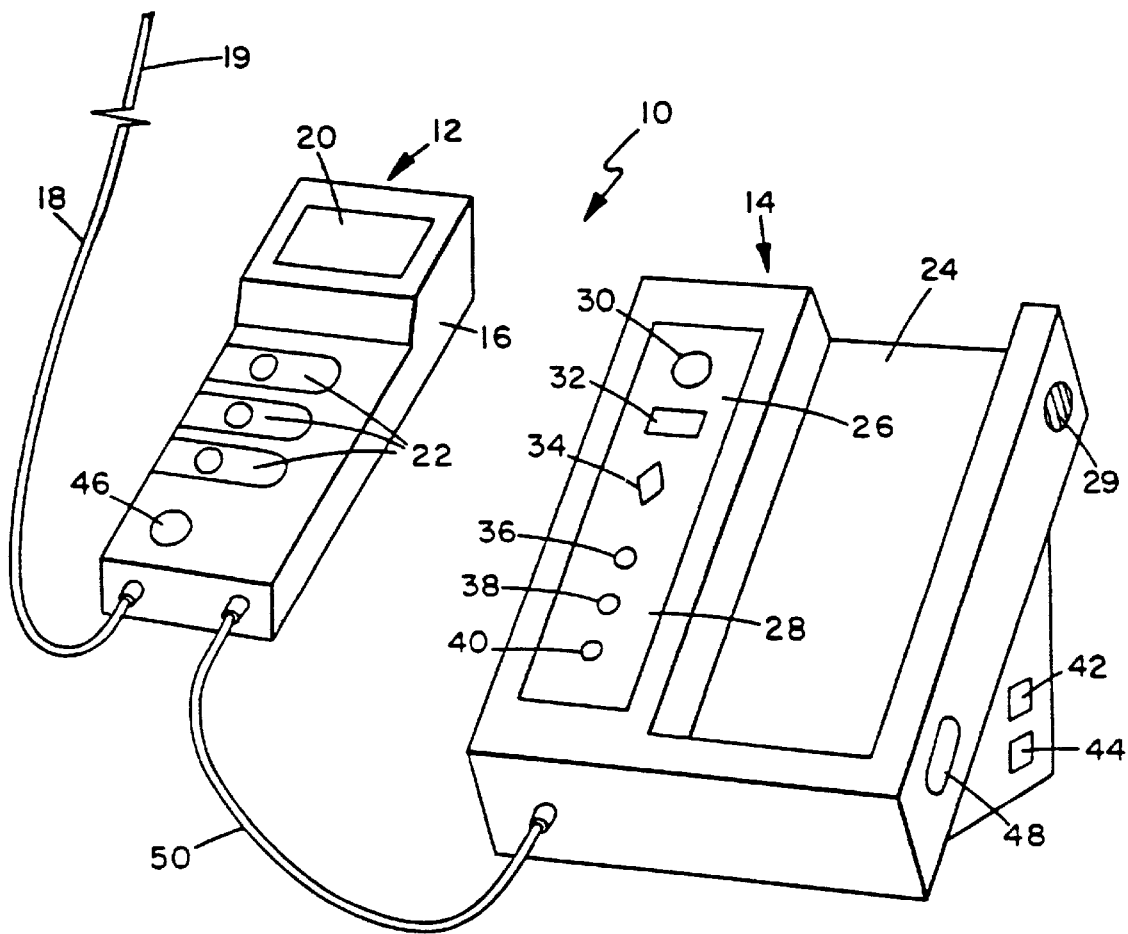
FIG. 1 is a diagrammatical representation of the programmable infusion system of the present invention.

An exemplary embodiment of the apparatus of the present invention is shown in FIG. 1 and is designated generally by reference numeral 10. As herein embodied and shown in FIG. 1, the remotely programmable infusion system 10 includes a pump unit 12 and a homebase 14. The pump unit 12 and homebase 14 may be two separate units, as illustrated in FIG. 1, or may comprise a single integral unit housing both the pump 12 and the homebase 14. With both elements integrated into a single infusion device, the device may be entirely portable and programmable, both via local and remote programming devices.

The pump unit 12 includes a housing 16 that contains the electrical and mechanical elements of the pump unit 12. An example of a pump unit 12 that can be used in the present invention is disclosed in U.S. Pat. No. 5,078,683, assigned to the assignee of the present invention. The pump unit 12 also includes an infusion line 18 that is connected to a patient at end 19. The pump unit 12 further includes a display 20 and various controls 22.

The homebase 14 includes a cradle 24 for holding the pump unit 12, a cable for connecting the homebase 14 to the pump unit 12, controls 26 for controlling operation of the homebase 14, display lights 28 for indicating various conditions of the homebase 14, and an internal audio device 29 for providing audio alarm signals. As embodied herein, the controls 26 include a link button 30, a local button 32, and a send button 34. The display lights 28 include a wait light 36, a phone light 38, and an alarm light 40. The function of the controls 26 and the display lights 28 will be described in detail below. The homebase 14 also includes a remote communication port 42 and a local communication port 44. Preferably, the homebase 14 and pump 12 are interconnected by an infra-red communications link 46, 48.

As embodied herein, the remote communication port 42 and the local communication port 44 each comprise a standard modem, as is well known in the art. Preferably, the modem module of the present invention is a Cermetek modem No. CH1785 or CH1782. These modem modules may operate at 2400 baud or other baud rates. Other baud rates, however, can also be employed in the present invention. The local button 32 is used to activate the local communication port 44. For example, when the care provider is at the premises where the infusion system 10 is located, the care provider presses the local button 32, thereby activating the local communication port 44. The care provider can then communicate with the homebase 14 via a local telephone (not shown) at the premises that is connected to the local communication port 44. If, on the other hand, the care provider is at a location remote from the infusion system 10, the link button 30 is pressed, activating the remote communication port 42. In this way, the care provider can communicate with the homebase 14 via a telephone (or other such transceiver) located at the remote location.

For convenience, this description refers to local and remote telephones, but it should be understood that any touch-tone or DTMF transceiver can be employed in the present invention, or for that matter, any transceiver that is capable of two-way communication and activation or selection of programming parameters both independently of and in response to various prompts and queries. It should also be understood that the term "touch-tone transceiver" is not limited to conventional push-button telephones having a 12 key keypad, with 0–9, "*", and "#" keys. Rather, as defined herein, the term "touch-tone transceiver" refers to any transceiver capable of generating signals via a keyboard or other data entry system and thus is not limited to transceivers that generate DTMF signals, such as conventional telephones. Examples of "touch-tone transceivers" as defined herein include conventional push-button telephones, computers having a keyboard and/or mouse, transmitters that convert human voice to pulse or digital or analog signals, and pager transceivers.

The homebase data port 46 and pump data port 48 comprise a wireless emitter/detector pair. Preferably, data ports 46, 48 each comprise and infra-red emitter/detector, permitting wireless communication between the pump unit 12 and the homebase 14. Other wireless communications ports may be employed, however, or the pump unit 12 and the homebase 14 may have their data ports 46, 48 hard-wired together. As described above, moreover, the pump unit 12 and the homebase 14 may comprise a single unit, obviating the need for a wireless or hard-wired link between the two units. A power cable 50 is preferably employed to provide power to the pump unit 12 via the homebase 14. Alternatively, the pump unit 12 may have its own power cable coupled directly to the power source, as opposed to being connected through the homebase 14.

Figure 2:
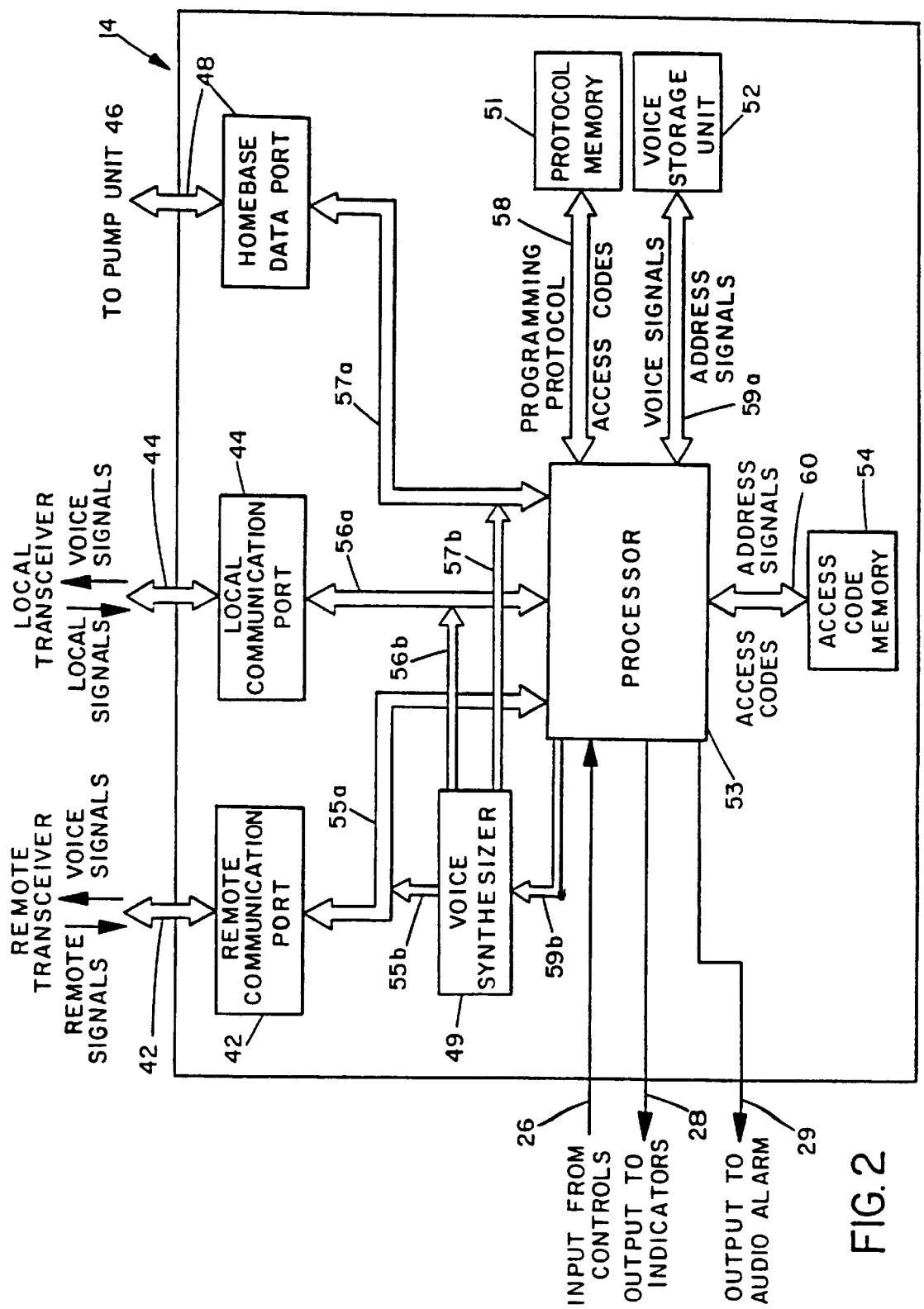
FIG. 2 is a block diagram of the homebase unit in accordance with the present invention.

With reference to FIG. 2, the elements included in the homebase 14 will be described. The homebase 14 comprises the remote communication port 42, the local communication port 44, a protocol memory 51, a voice storage unit 52, a processor 53, a voice synthesizer 49, and an access code memory 54. The protocol memory 51, the voice storage unit 52, and the access code memory 54 can all be contained in the same memory device (such as a random-access memory), or in separate memory units. Preferably, the voice storage unit 52 comprises a read-only memory (ROM), and the processor 53 comprises an 8-bit microcontroller, such as the Motorola MC68HC11A0FN. The homebase 14 also includes the data port 48 for relaying information between the homebase 14 and pump unit 12. The voice synthesizer 49 is preferably an integrated circuit that converts digitized voice signals to a signal that emulates the sound of a human voice. As embodied herein, the voice synthesizer 49 need only be used to convert the signals outgoing from the homebase 14 to the remote or local telephone and thus is not required for converting incoming signals from the remote or local telephone. The voice synthesizer may comprise an LSI speech synthesis chip commercially available from Oki, part number MSM6585.

The remote communication port 42, the local communication port 44, and the homebase data port 48 are all coupled to the processor 53 via data buses 55a, 56a, 57a, respectively. The communication ports 42, 44 receive signals from a transceiver (such as a telephone) and relay those signals over the buses 55a, 56a, respectively, to the processor 53, which in turn processes the signals, performing various operations in response to those signals. The processor 53 receives digitized voice signals from the voice storage unit 52 via bus 59a and sends those digitized voice signals to the voice synthesizer 49 via bus 59b, where the signals are converted human voice emulating signals. Those human voice signals are sent from the voice synthesizer 49 via buses 55b, 56b, 57b to buses 55a, 56a, 57a, which in turn relay the those signals to the remote communication port 42, the local communication port 44, and the homebase data port 48, respectively.

For example, suppose it is necessary to provide instructions to the care provider operating the remote telephone (not shown). The processor 53 sends a voice address signal over a data bus 59a coupling the processor 53 to the voice storage unit 52. The voice address signal corresponds to a location in the voice storage unit 52 containing a particular voice signal that is to be sent to the remote transceiver. Upon receiving the voice address signal, the particular voice signal is accessed from the voice storage unit 52 and sent, via the data bus 59a, to the processor 53. The processor 53 then relays the voice signal via the data bus 59b to the voice synthesizer 49, which converts the voice signal and sends the converted signal via data buses 55b and 55a to the remote communication port 42, which sends the converted signal to the remote transceiver. The voice signal retrieved from the voice storage unit 52 may be a digitized representation of a person's voice or a computer generated voice signal (both being well known in the art). The digitized voice signal is converted by the voice synthesizer 49 to a signal that emulates the sound of a human voice. The voice signal instructs the care provider on how to respond to the voice signal and what type of information the care provider should send. As the remote transceiver may be a push-button telephone having a keypad with multiple keys, the care provider then presses the appropriate key or keys, thereby sending a DTMF signal back to the remote communication port 42 of the homebase 14. It should be understood, however, that the remote transceiver need not be a push-button telephone, but rather any transceiver capable of sending and receiving DTMF or other similar signals. For example, the remote transceiver may be a computer or portable remote controller.

Suppose the DTMF signal sent by the care provider is a remote programming signal, which is transmitted from the remote telephone to the remote communication port 42 of the homebase 14. The remote communication port 42 then relays the remote programming signal via the data bus 55*a* to the processor 53. In response to receiving the remote programming signal, the processor 53 accesses a particular parameter of the programming protocol from the protocol memory 51. To access the parameter, the processor 53 transmits a protocol address signal over the data bus 58 that couples the processor 53 and the protocol memory 51. The protocol address signal corresponds to a location in the protocol memory 51 containing the parameter. The parameter is then sent from the protocol memory 51 to the processor 53 over the data bus 58. Depending on the nature of the remote programming signal, the processor 53 can then perform one of a number of operations on the parameter, including editing, erasing, or sending the parameter back to the remote transceiver for review. Those skilled in the art will recognize that many types of signals or commands can be sent from the remote transceiver to the homebase 14 for processing. Examples of such signals, how they are processed, and their effect will be described in detail below in conjunction with the description of the operation of the present invention.

In accordance with the present invention, the infusion system 10 can incorporate various security measures to protect against unwanted programming of the pump protocol. Significantly, a user access code can be used to block programming except by persons with the user access code, which may be a multi-digit number (preferably a four digit number). The infusion system 10 can be equipped with one or multiple user access codes, which are stored in the access code memory. To initiate communication with the infusion system 10, a care provider is connected to the infusion system 10 via a remote conventional push-button telephone (not shown). This connection may be initiated by a call from the care provider to the infusion system 10 (or a patient talking on a telephone located near the infusion system 10), or by a call from the patient to the care provider. Either way, the care provider is connected to the infusion system 10. After the connection is made between the care provider and the infusion system 10, the care provider is asked (via a voice signal stored in the voice storage unit 52) to enter the user access code. If the care provider enters a valid user access code (as explained above, there may be several valid codes), the care provider is permitted to access and/or program the pump protocol.

During a programming session, in certain circumstances (which will be described below), the user access codes can be reviewed, edited, and/or erased entirely and re-entered. To perform any of these functions, a programming signal is sent by the care provider (from, e.g., a remote push-button telephone) to the homebase 14. That programming signal is relayed by the remote communication port 42 to the processor 53, which processes the signal and generates an access code address signal. The access code address signal, which corresponds to a memory location in access code memory 54 holding a user access code, is sent over a data bus 60 to the access code memory 54. The particular user access code is then retrieved and sent back over the data bus 60 to the processor 53, which processes the user access code in some manner.

To communicate with the pump 12, the homebase is equipped with the homebase data port 48. The pump protocol can be sent from the homebase 14 to the pump 12 via the homebase data port 48 and the pump data port 46. Thus, for example, the processor 53 accesses the protocol from the protocol memory 51 and sends the protocol via data bus 57*a* to the homebase data port 48. The homebase data port 48 then sends the information over the infra-red link to the pump data port 46, where it is processed by circuitry and/or software in the pump 12. In this way, the pump protocol can be programmed (e.g., edited, redone, reviewed, locked, re-entered, etc.).

The functions of the controls 26 of the infusion system 10 will now be described. The local button 32 is used to activate the local transceiver. If the care provider is located at the homebase 14, and a local transceiver (e.g., a push-button telephone) is at that location and connected to the local communication port 44, the local button 32 is depressed, activating the local communication port 44 and thereby providing a communication connection between the local telephone and the homebase 14.

The send button 34 is designed to permit sending of the infusion system 10 protocol to a remote (or local) computer (not shown). In this way, a remote or local computer can maintain a file having the protocol of many infusion systems 10 located in various places and monitor those protocols. If the computer is remote from the infusion system 10, a person located at the homebase 14 presses the send button 34, which in turn downloads the existing protocol to the remote communication port 42. The protocol is then transmitted via the remote communication port 42 to the remote computer.

The link button 30 is used to initiate a remote (or local) programming session, or, in other words, to enter the remote touch-tone programming mode of the infusion system 10. When initiating a programming session, the care provider calls the telephone number corresponding to the infusion system 10 (or the patient's home phone). The call may ring at a local telephone coupled to the homebase 14 via the local communication port 44. The patient answers the call, and the care provider and patient can communicate between the remote and local telephones via standard voice signals. This is known herein as a phone mode or patient conversation mode. The care provider then instructs the patient to depress the link button 30, which disconnects the patient from the telephone line and initiates the programming mode described below with reference to FIGS. 3–9. If, however, the patient does not answer the care provider's call, the homebase may be equipped with an internal switching system that directly connects the care provider with the homebase 14 and initiates the programming mode. The internal switching may be accomplished with hardware in the homebase 14 or with software that controls the processor 53, or with a hardware-software combination. Either way, the care provider may then begin processing the information and protocol stored in the homebase 14. (As described above, the call may be initiated by the patient to the care provider.)

The functions of the display lights 28 will now be described. Preferably, the display lights 28 comprise LEDs. The wait light 36 indicates when the homebase 14 is involved in a programming session or when its is downloading the protocol to the remote computer. Accordingly, the wait light 36 tells the patient not to disturb the homebase 14 until the wait light 36 goes off, indicating that internal processing elements of the homebase 14 are inactive. The phone light 38 indicates when the care provider and the patient are involved in voice communication via the remote telephone and the local telephone and thus when the internal processing elements of the homebase 14 are inactive. The phone light 38 may also indicate when the infusion system 10 is ready. The alarm light 40 indicates various alarm conditions and functions in the infusion system 10. The alarm conditions and operation of the alarm light in response to those conditions will be described below with reference to FIG. 10.

Illustrated in FIGS. 3–9, the programming mode or sequence of the present invention will be described in detail. As described above, when a care provider wants to access and process the protocol of the homebase 14 from a remote telephone, the care provider calls a telephone number corresponding to the infusion device 10. Preferably, the call from the care provider rings at a local telephone coupled to the homebase 14. If the call is answered by the patient (or some other person) located at the local telephone and homebase 14, the care provider and patient communicate by standard voice signals between the remote and local telephones (i.e., communicate in the phone or patient conversation mode). During such communications, the care provider asks the patient to depress the link button 30 (or some series of buttons) on the homebase 14, which connects the care provider with homebase 14, terminates the phone mode, and initiates a remote touch-tone programming session. If, on the other hand, the care provider's call is not answered, the care provider may be directly connected to the homebase 14, as described above, thereby directly initiating a remote touch-tone programming session without entering the phone mode. Alternatively, a touch-tone programming session can be initiated by a care provider located at the local push-button telephone simply by picking up the telephone handset and pressing the local button 32, which gives the local telephone access to the homebase 14.

Once the care provider has accessed the programming mode of the homebase 14, a series of steps are followed to enable the care provider to program the operational protocol of the infusion device 10. It should be understood that the following programming and access steps are exemplary only and that many variations can be made to the disclosed scheme.

Figure 3:
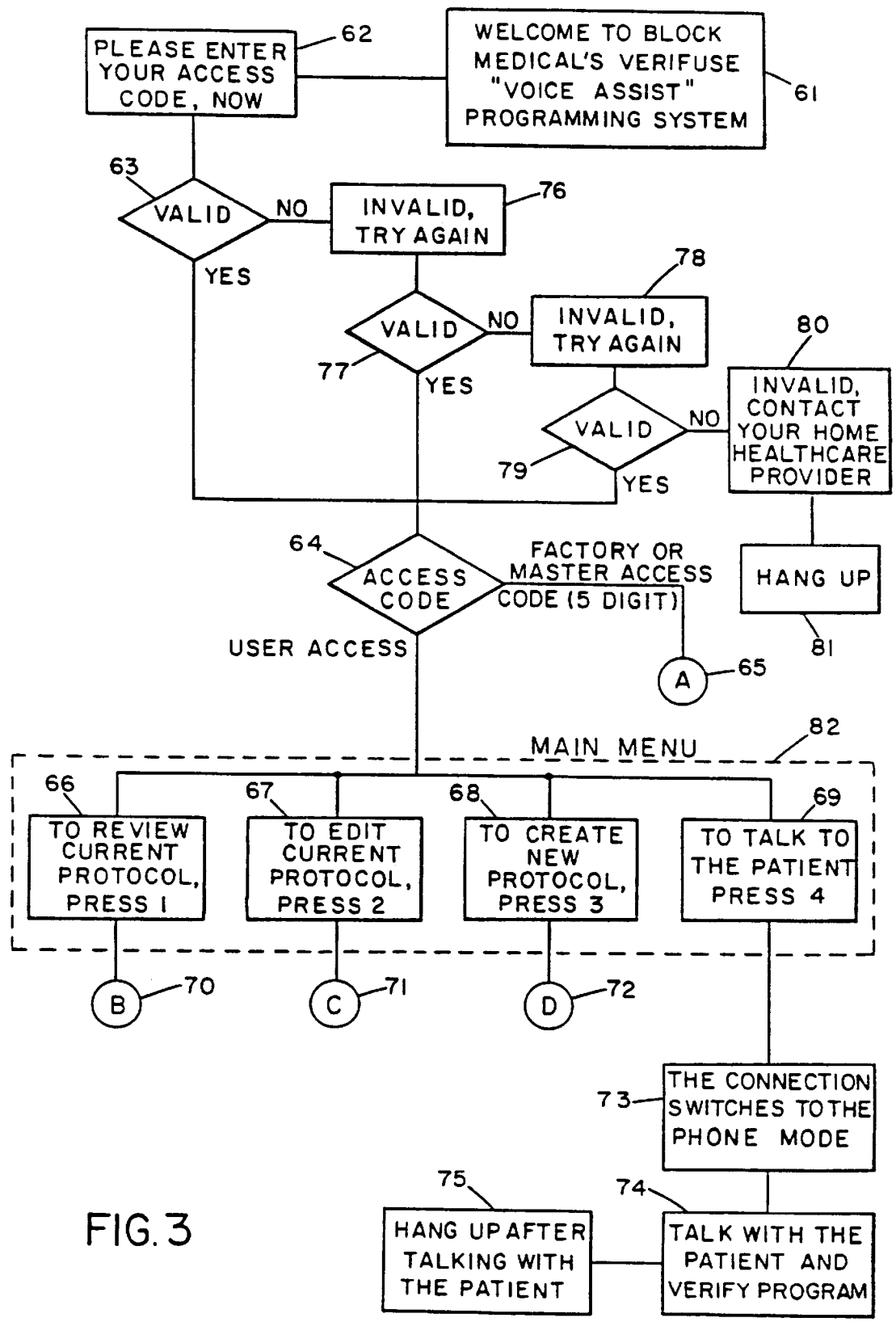
FIG. 3 is a flow diagram illustrating entry of an access code and the main menu in an example of the present invention.

With reference to FIG. 3, the processor 53 accesses from the voice storage unit 52 a greeting message 61, which is transmitted to the care provider at the remote or local telephone. Following the greeting message 61, a voice command 62 (which is accessed by the processor 53 from the voice storage unit 52) is sent to the care provider asking the care provider to enter an access code. Using the keys on the remote push-button telephone, the care provider enters the access code, and the processor 53 determines whether the entered access code is valid (Step 63). If it is valid, the processor 53 determines in Step 64 whether it is a master access code or a user access code. If the care provider has entered a master access code, the care provider is transferred (circle 65) to an access code menu 90 illustrated in FIG. 4, which provides for programming of the master and user access codes.

If the care provider has entered a user access code, the processor 53 accesses from the voice storage unit 52 a number of voice queries comprising a main menu 82: (1) Step 66—asks whether the care provider wants to review the current programmable homebase protocol, instructing the care provider to depress a particular key on the touch-tone key pad to select this option; (2) Step 67—asks whether the care provider wants to edit the current protocol, providing a similar instruction; (3) Step 68—asks whether the care provider wants to create an entirely new protocol, with instructions on how to select this option; and (4) Step 69—asks whether the care provider wants to terminate the programming session and return to voice communication with the patient. If the care provider selects the review mode (Step 66), the care provider is transferred (circle 70) to a review mode menu 195 illustrated in FIG. 5. If the care provider selects the edit mode (Step 67), the care provider is transferred (circle 71) to an edit mode menu 200 illustrated in FIG. 6. If the care provider selects the create mode (Step 68), the care provider is transferred (circle 72) to a create mode menu 300 illustrated in FIG. 8A. Finally, if the care provider selects direct conversation with the patient (Step 69), the connection is switched to a phone mode (Step 73). In the phone mode, the care provider can talk with the patient to verify programming changes (Step 74). The care provider can then hang up the remote telephone after completing the conversation with the patient (Step 75).

If the care provider entered an invalid access code, the following steps are followed. In response to receiving an invalid code (see Step 63), the care provider is asked (in Step 76) to enter another access code because the one previously entered was invalid. If this next entered access code is valid, the care provider is transferred (via Step 77) to the access code decision step (i.e., Step 64), and the process is as described above. If, however, the care provider enters another invalid access code, decision Step 77 goes to Step 78, in which the care provider is told the access code is invalid and is asked to enter another access code. If this code is valid, decision Step 79 transfers the care provider to access code decision step 64. If, on the other hand, the care provider has entered a third invalid access code, decision Step 79 goes to Step 80. The care provider is told in Step 80 that the access code is invalid and to contact a home healthcare provider to obtain a correct access code, and the homebase 14 hangs up (Step 81). It should be understood that any number of iterations of access code entering can be employed in the present invention. For example, if the care provider enters two invalid access codes, the homebase could hang up, or it could permit the care provider more than three tries to enter a proper access code.

Figure 4:
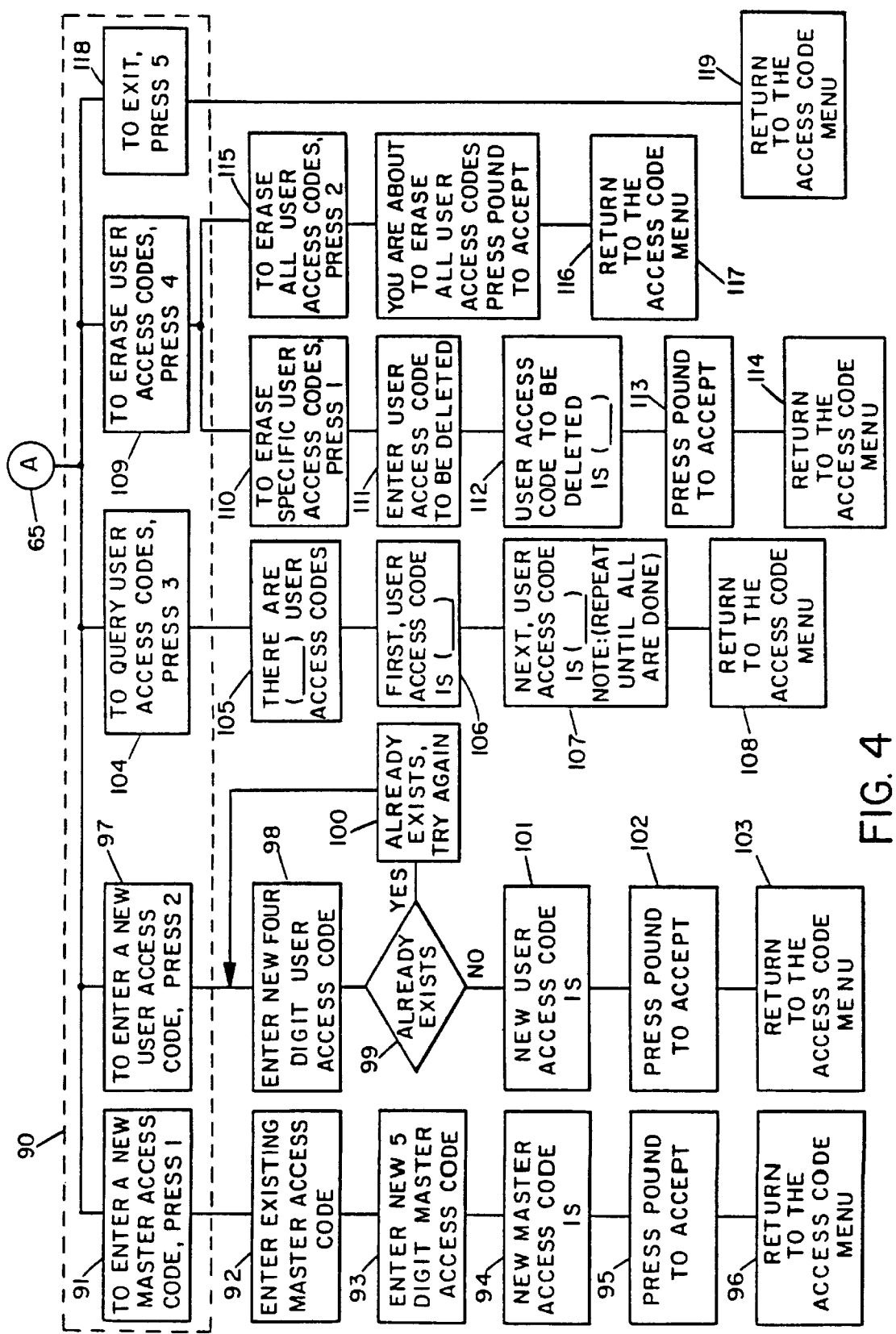
FIG. 4 is a flow diagram illustrating an access code menu in accordance with an example of the present invention.

Referring now to FIG. 4, the access code menu 90 will be described. If the care provider has entered a master access code, the care provider is transferred to the access code menu 90 (via circle 65). Upon accessing this menu, the homebase 14 generates a number of voice queries that are transmitted to the care provider and provide the care provider with a number of options. First, in Step 91, the care provider is asked whether a new master access code is to be entered and is instructed to press a certain button on the touch tone key pad (in this case the number "1") to select this option. If the care provider selects this option, the homebase 14 tells the care provider to enter the existing master access code (Step 92) and to enter a new master access code (Step 93). The newly entered master access code is then read back to the care provider by the homebase 14 (Step 94), and the homebase 14 generates a voice command that tells the care provider to press the "#" key on the key pad to accept this new master access code (Step 95). If the care provider presses the "#" key, the homebase 14 returns (Step 96) the care provider to the access code menu 90 (via circle 65). Those skilled in the art will recognize that the keys to be pressed by the care provider are only exemplary and that other keys could be designated to accept and/or select various options and programming entries.

Second, in Step 97, the care provider is asked whether a new user access code is to be entered and is instructed to press a certain button on the touch tone key pad (in this case the number "2") to select this option. If the care provider selects this option, the homebase 14 tells the care provider to enter a new user access code (Step 98). If the entered new user access code already exists, the program loops around (Steps 99–100) and asks the care provider to enter a new master access code again (Step 97). If the newly entered user access code does not already exist, the new user access code is then read back to the care provider by the homebase 14 (Step 101), and the homebase 14 generates a voice command that tells the care provider to press the "#" key on the key pad to accept this new user access code (Step 102). If the care provider presses the "#" key, the homebase 14 returns (Step 103) the care provider to the access code menu 90 (via circle 65).

Third, in Step 104, the care provider is asked whether he or she would like to query the user access codes and is instructed to press a certain button on the touch tone key pad (in this case the number "3") to select this option. If the care provider selects this option, the homebase 14 tells the care provider in Step 105 that there are a certain number of user access codes (depending on how many there are). In Step 106, the homebase 14 recites the user access codes to the care provider and continues reciting the user access codes (Step 107) until all are recited. After completing reciting the user access codes, the homebase 14 returns (Step 108) the care provider to the access code menu 90 (via circle 65).

Fourth, in Step 109, the care provider is asked whether he or she would like to erase the user access codes and is instructed to press a certain button on the touch tone key pad (in this case the number "4") to select this option. If the care provider selects this option, the homebase 14 asks the care provider to select one of two options: (1) to erase specific user access codes, press a certain button on the touch-tone key pad (in this case the number "1") (see Step 110); or (2) to erase all user access codes, press a different button (in this case the number "2") (see Step 115). If the care provider selects Step 110, the care provider is asked to enter the specific user access code to be deleted (Step 111), and the homebase 14 reads back that specific user access code in Step 112. The homebase 14 then asks the care provider to press the "#" button on the touch-tone key pad to accept deletion of that user access code (Step 113) and is returned to the access code menu in Step 114. If the care provider selects Step 115 (global deletion), the homebase 14 warns the care provider that he or she is about to erase all the user access codes and asks for the care provider to press the "#" button to accept (Step 116). The homebase then returns to the access code menu 90 (Step 117).

Fifth, in Step 118, the care provider is asked to press a certain number (in this case "5") to exit the access code menu. If the care provider selects this option, the homebase 14 returns (via Step 119) to the access code prompt 62 (see FIG. 3).

Figure 5B:
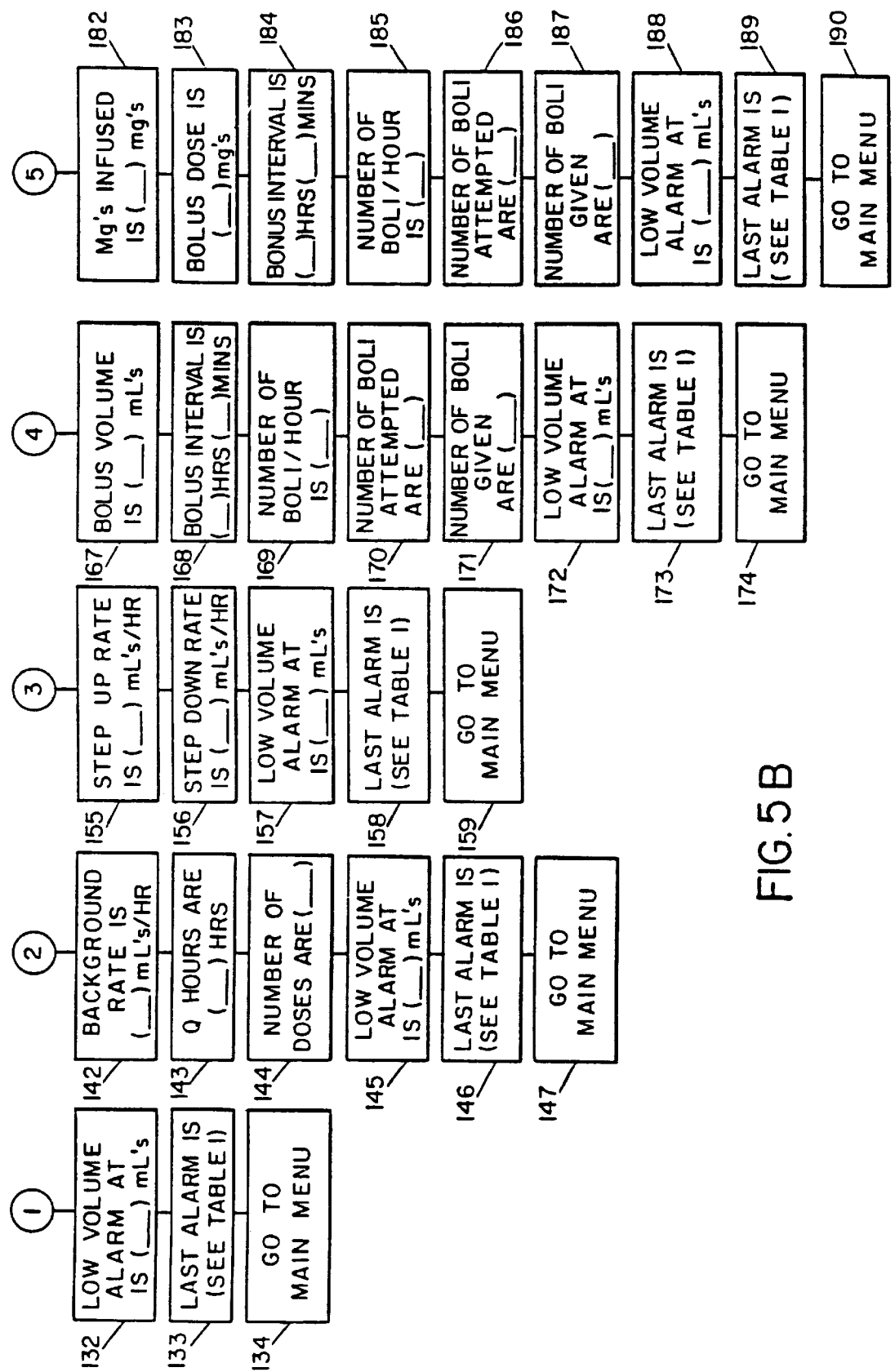

Referring now to FIGs. 5A and 5B, the review mode will be described in detail. If the care provider has selected the review mode in Step 66, the homebase 14 transfers (circle 70) the care provider to a review mode menu 195 illustrated in FIG. 5A. Upon accessing this menu, the homebase 14 generates a number of voice queries that are transmitted to the care provider and provide the care provider with a number of options—namely, reviewing the following information: (1) the operating parameters of a continuous mode of the pump 12 (Step 120); (2) the operating parameters of an intermittent mode of the pump 12 (Step 121); (3) the operating parameters of a taper mode of the pump 12 (Step 122); (4) the operating parameters of a patient controlled analgesia (PCA) mode in milliliters (mL) of the pump 12 (Step 123); and (5) the operating parameters of a PCA mode in milligrams (mg) of the pump 12 (Step 124). The continuous mode refers to a pump that continually delivers fluid to the patient, whereas the intermittent mode refers to intermittent delivery of fluids. The taper mode refers to a mode in which fluid delivery is stepped-up to a base rate then stepped-down to a "keep vein open" rate periodically during administration. The PCA mode refers to the ability of the patient to self-administer an additional burst (or "bolus") of the fluid being administered by the pump. In other words, when the present dosage of analgesia being administered to the patient by the pump is inadequate to relieve pain, the patient can self-administer a bolus shot to bolster the dosage being automatically delivered by the pump.

If the care provider selects review of the continuous mode (Step 120), the homebase 14 provides the care provider with a variety of information. The care provider is told whether the protocol is locked or unlocked (Step 125); whether the "air-in-line" (AIL) alarm is on or off (Step 126); the elapsed time in hours, minutes, and/or seconds of the present administration to the patient (Step 127); the programmed rate of fluid being delivered in mLs per hour (Step 128); the current rate of fluid in mLs per hour (Step 129); the volume of fluid to be infused in mLs (Step 130); the volume of fluid already infused (Step 131); the level in mLs at which the low volume alarm will sound (Step 132); and the last occurrence of the alarm (Step 133). (See also FIG. 10, which illustrates the alarm table.) After providing this information to the care provider, the homebase 14 in Step 134 returns to the main menu 82.

If the care provider selects review of the intermittent mode (Step 121), the homebase 14 also provides the care provider with a variety of information. Steps 135–137 provide the same information as Steps 125–127, respectively. Step 141 provides the same information as Step 131, and Steps 145–146 provide the same information as Steps 132–133, respectively. Additional information provided to the care provider in the intermittent mode is as follows: the programmed dose rate of fluid being delivered in mLs per hour (Step 138); the current dose rate of fluid in mLs per hour (Step 139); the dose volume of fluid to be infused in mLs (Step 140); the background rate in mLs per hour (Step 142); the time between doses (or "Q" hours) (Step 143); and the number of doses (Step 144). After providing this information to the care provider, the homebase 14 returns in Step 147 to the main menu 82.

If the care provider selects review of the taper mode (Step 122), the homebase 14 also provides the care provider with a variety of information. Steps 148–150 provide the same information as Steps 125–127, respectively. Step 154 provides the same information as Step 131, and Steps 157–158 provide the same information as Steps 132–133, respectively. Additional information provided to the care provider in the taper mode is as follows: the programmed base rate of fluid being delivered in mLs per hour (Step 151); the current base rate of fluid in mLs per hour (Step 152); the volume of fluid before taper down in mLs (Step 153); the step-up rate in mLs per hour (Step 155); and the step-down rate in mLs per hour (Step 156). After providing this information to the care provider, the homebase 14 returns in Step 159 to the main menu 82.

If the care provider selects review of the PCA mL mode (Step 123), the care provider is also given information. Steps 160–162 provide the same information as Steps 125–127, respectively. Steps 165–166 provide the same information as Steps 130–131, respectively, and Steps 172–173 provide the same information as Steps 132–133, respectively. Additional information provided to the care provider in the PCA mL mode is as follows: the programmed continuous rate of fluid being delivered in mLs per hour (Step 163); the current continuous rate of fluid in mLs per hour (Step 164); the bolus volume of fluid in mLs (Step 167); the bolus interval in hours and minutes (Step 168); the number of boli/hour (Step 169); the number of boli attempted (Step 170); and the number of boli delivered (Step 171). After providing this information to the care provider, the homebase 14 returns in Step 174 to the main menu 82.

If the care provider selects review of the PCA mg mode (Step 124), the care provider is given other information. Steps 175–177 provide the same information as Steps 125–127, respectively, and Steps 188–189 provide the same information as Steps 132–133, respectively. Additional information provided to the care provider in the PCA mg mode is as follows: the concentration of fluid delivered in mg/mL (Step 178); the programmed continuous rate of fluid in mgs/hour (Step 179); the current continuous rate in mg's/hour (Step 180); the mgs to be infused (Step 181); the mgs infused in mgs (Step 182); the bolus dose in mgs (Step 183); the bolus interval in hours and minutes (Step 184); the number of boli/hour (Step 185); the number of boli attempted (Step 186); and the number of boli delivered (Step 187). After providing this information to the care provider, the homebase 14 returns in Step 190 to the main menu 82.

Figure 6A:
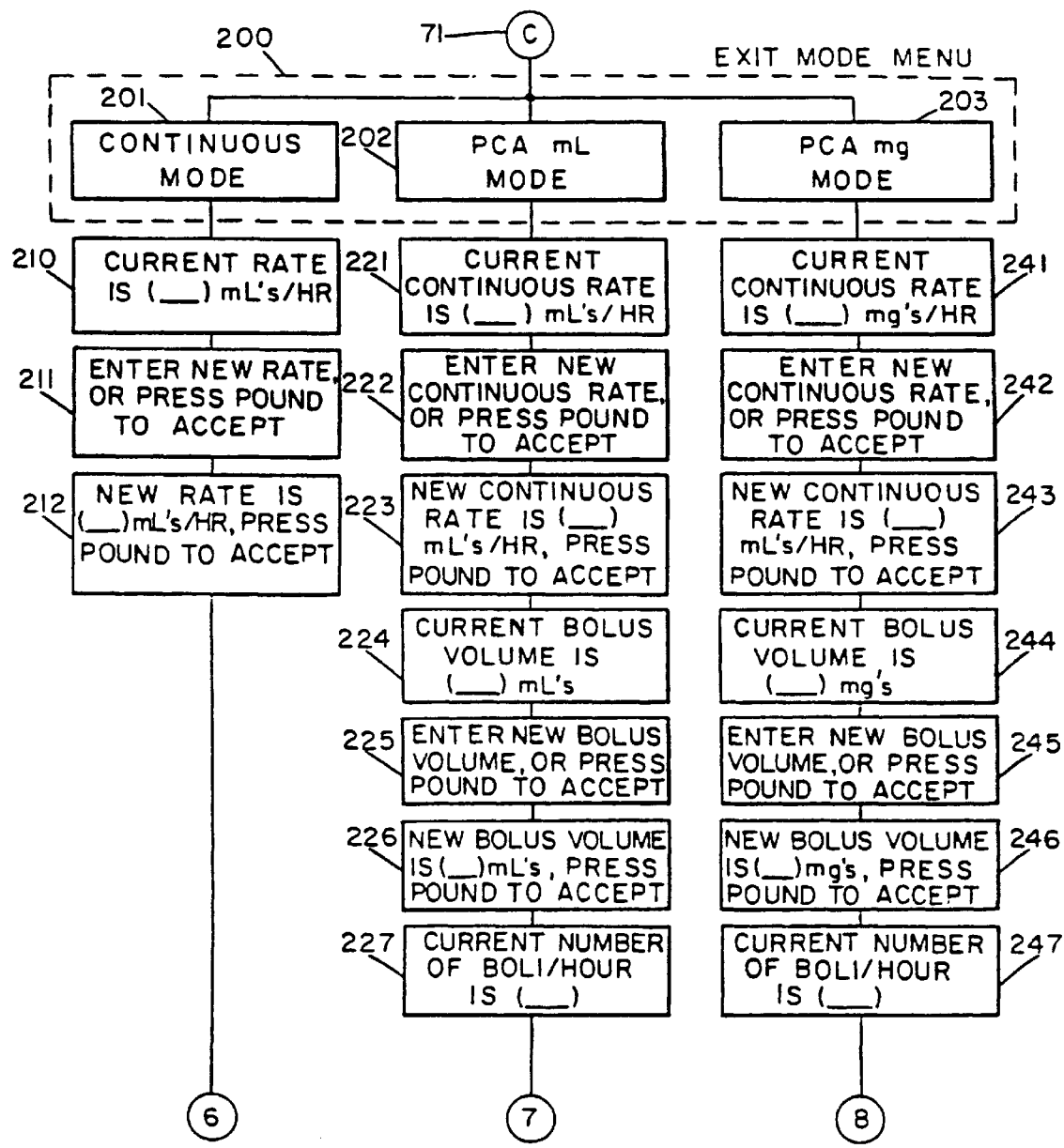
FIGS. 6A and 6B represent a flow diagram illustrating an edit mode menu in accordance with an example of the present invention.
Figure 6B:
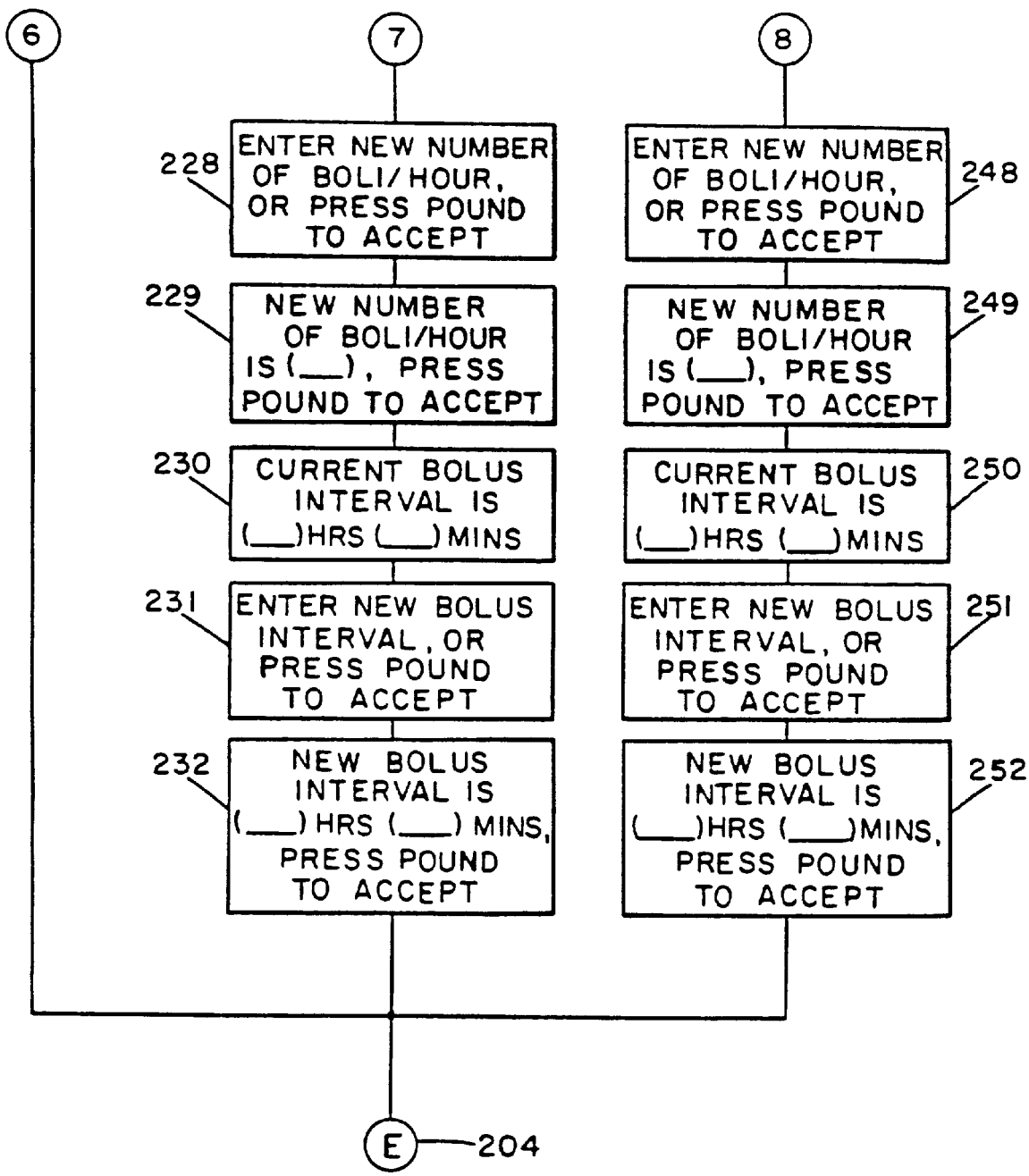

With reference to FIGS. 6A and 6B, the edit mode will be described in detail. If the care provider has selected the edit mode in Step 67, the homebase 14 transfers (circle 71) the care provider to an edit mode menu 200 illustrated in FIG. 6A. Upon accessing this menu, the homebase 14 generates a number of voice queries that are transmitted to the care provider and provide the care provider with a number of options—namely: (1) editing the operating parameters of the continuous mode (Step 201); (2) editing the operating parameters of PCA mL mode (Step 202); and (3) editing the operating parameters of the PCA mg mode (Step 203). No matter which option is selected, after editing the operating parameters (or protocol) of that mode, the care provider is transferred (see circle 204 in FIG. 6B) to the edit mode sub-menus 270, 280 illustrated FIG. 7.

If the care provider selects editing of the continuous mode (Step 201), the homebase 14 permits the care provider to edit the rate of delivery. In this mode, some parameters are maintained and others may be edited. The care provider is told the current rate at which the pump 12 is delivering fluid in mLs/hour (Step 210). The care provider is then asked to enter a new rate, or press the "#" button to accept the current rate (Step 211). Finally, the care provider is told the new rate in mLs/hour and is asked to press the "#" button on the key pad to accept the new rate (Step 212). After the rate has been edited, the homebase 14 transfers (circle 204) to the sub-menus 270, 280 of FIG. 7.

If the care provider selects editing of the PCA mL mode (Step 202), the care provider is asked to edit various parameters of the PCA mL protocol. The care provider is first told what the current continuous rate is in mLs/hour (Step 221), and in Step 222 is asked to enter a new continuous rate or press the "#" button to accept the present rate. The care provider is then told what the new rate is and asked to press the "#" button to accept that new rate (Step 223). Similar operations are performed on the bolus volume (Steps 224–226), the number of boli/hour (Steps 227–229), and the bolus interval (Steps 230–232). After editing, the homebase 14 transfers (circle 204, as shown in FIG. 6B) to the sub-menus 270, 280 of FIG. 7.

If the care provider selects editing of the PCA mg mode (Step 203), the care provider is asked to edit various parameters of the PCA mL protocol. The care provider is first told what the current continuous rate is in mgs/hour (Step 241), and in Step 242 is asked to enter a new continuous rate or press the "#" button to accept the present rate. The care provider is then told what the new rate is and asked to press the "#" button to accept that new rate (Step 243). Similar operations are performed on the bolus volume (Steps 244–246), the number of boli/hour (Steps 247–249), and the bolus interval (Steps 250–252). After editing, the homebase 14 transfers (circle 204) to the sub-menus 270, 280 of FIG. 7.

Figure 7:
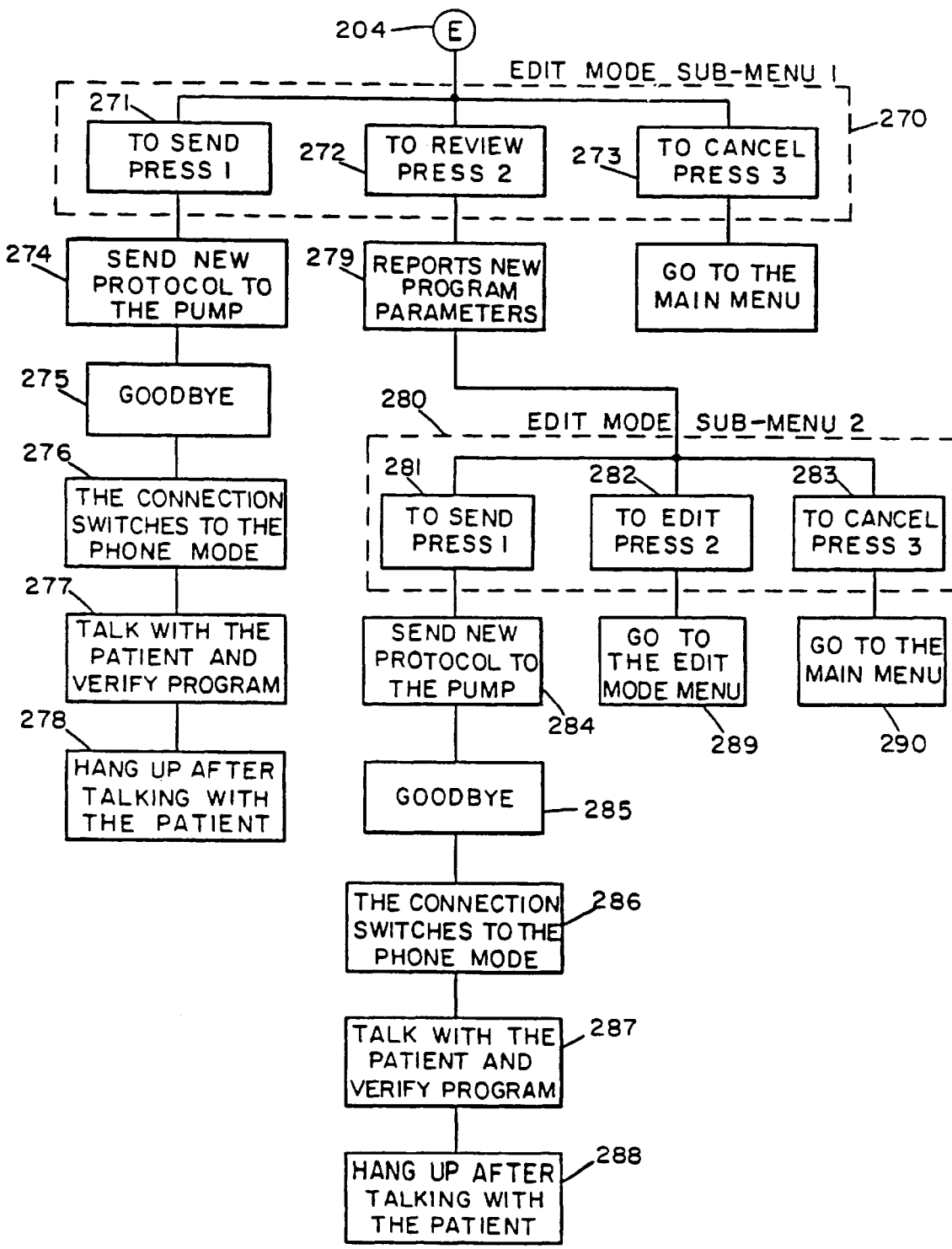
FIG. 7 is a flow diagram illustrating sub-menus of the edit mode menu in accordance with an example of the present invention.

Referring now to FIG. 7, the edit mode sub-menus 270, 280 provide the care provider with several options after editing the protocol. The first edit mode sub-menu 270 allows the care provider to send (i.e., save) the edits to the pump 12 (Step 271) by pressing a certain key on the key pad (in this case "1"), to review the edits (Step 272) by pressing a different key on key pad (in this case "2"), and to cancel the edits (Step 273) by pressing still a different number on the key pad (in this case "3"). If the care provider selects sending the edits (Step 271), the new protocol is sent to the pump 12 (Step 274), and the care provider is told "goodbye" (Step 275). The care provider is then transferred to the phone or patient conversation mode (Step 276), and the care provider is put in connection with the patient to verify the programming (Step 277). After verifying the programming changes with the patient, the care provider hangs up the remote telephone (Step 278), and the programming session is terminated.

If the care provider selects reviewing the edits (Step 272), the homebase 14 reports the new parameters of the protocol to the care provider (Step 279). After reporting, the care provider is taken to the second edit mode sub-menu 280. The second edit mode sub-menu 280 permits the care provider to select one of several options: (1) send the edits by pressing a key on the key pad (Step 281), (2) edit the edits by pressing a different key on the key pad (Step 282), or (3) cancel the edits by pressing still a different key on the key pad (Step 283). If the care provider selects sending the edits (Step 281), the new protocol is sent to the pump 12 (Step 284), and the care provider is told "goodbye" (Step 285). The care provider is then transferred to the phone or patient conversation mode (Step 286), and the care provider is put in connection with the patient (the patient conversation mode) to verify the programming (Step 287). After verifying the programming changes with the patient, the care provider hangs up the remote telephone (Step 288), and the programming session is terminated. If the care provider selects editing of the edits (Step 282), the care provider is transferred to the edit mode menu (Step 289) illustrated in FIG. 7 and described above. If the care provider selects cancelling of the edits (Step 283), the care provider is transferred to the main menu 82 (Step 290).

Figure 8B:
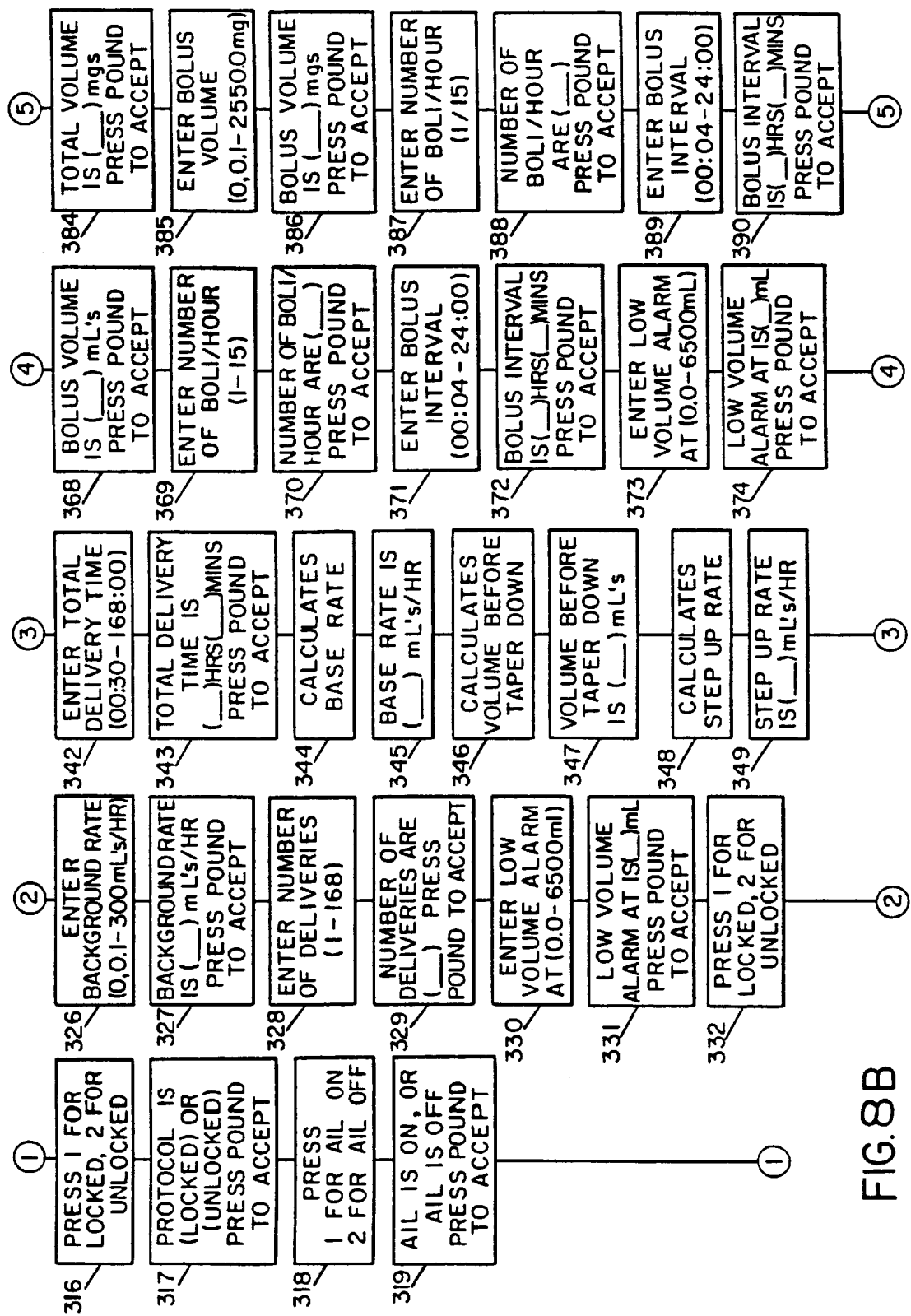
Figure 8C:
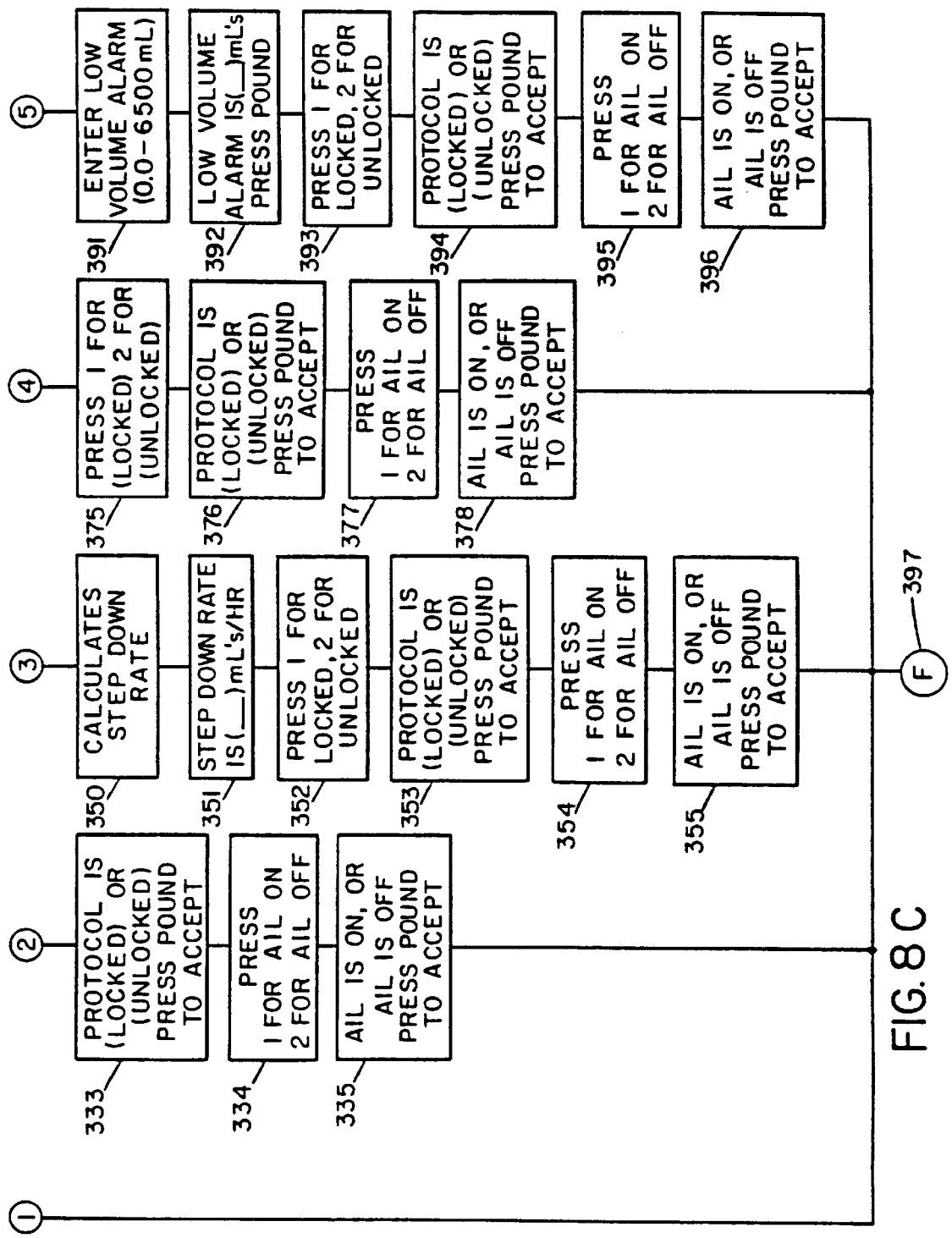

With reference to FIGS. 8A, 8B and 8C, the create mode will now be described. If the care provider selects the create mode in Step 68, the homebase 14 transfers the care provider to a create mode menu 300. Within the create mode menu 300, the care provider has several options for processing the protocol: (1) the continuous mode 302, (2) the intermittent mode 304, (3) the taper mode 306, and (4) the PCA mode 308. For any of these modes to be selected, the care provider presses a predetermined number on the keypad of the remote programming transceiver or push-button telephone.

If the care provider selects programming of the continuous mode 302 from the create mode menu 300, the care provider is asked to program various parameters of the continuous mode protocol. The care provider is asked to enter the rate (Step 310), after which the entered rate is read back, and the care provider is asked to press the "#" button to accept this rate (Step 311). The care provider follows the same procedure for entering volume (Steps 312 and 313), low volume alarm (Steps 314 and 315), protocol locking (Steps 316 and 317), and AIL on or off (Steps 318 and 319). After programming, the care provider is transferred (circle 397) to the sub-menus of FIG. 9.

If the care provider selects programming of the intermittent mode 304, the care provider is asked to program various parameters of the intermittent mode protocol. The care provider is asked to enter the number of "Q" hours (Step 320), after which the entered number of "Q" hours is read back, and the care provider is asked to press the "#" button to accept this number (Step 321). The care provider follows the same procedure for entering dose rate (Steps 322 and 323), dose volume (Steps 324 and 325), background rate (Steps 326 and 327), number of deliveries (Steps 328 and 329), low volume alarm (Steps 330 and 331), protocol locking (Steps 332 and 333), and AIL on or off (Steps 334 and 335). After programming, the care provider is transferred (circle 397) to the sub-menus of FIG. 9.

If the care provider selects programming of the taper mode 306, the care provider is asked to program various parameters of the taper mode protocol. The care provider is asked to enter the total volume (Step 336), after which the entered total volume is read back, and the care provider is asked to press the "#" button to accept (Step 337) this volume. The care provider follows the same procedure for entering taper up time (Steps 338 and 339), taper down time (Steps 340 and 341), and total delivery time (Steps 342 and 343). The homebase unit 14 then calculates the base rate (Step 344) and reads this base rate back to the care provider (Step 345); calculates the volume before taper down (Step 346) and reads this volume back to the care provider (Step 347); and calculates the step up and step down rates (Steps 348 and 350) and reads these back (Steps 349 and 351). The care provider is also asked to enter protocol locking (Steps 352 and 353) and AIL on or off (Steps 354 and 355). After programming, the care provider is transferred (circle 397) to the sub-menus of FIG. 9.

If the care provider selects programming of the PCA mode 308, the care provider is taken to a PCA mode sub-menu 360. In the PCA mode sub-menu 360, the care provider is asked to select the PCA mL mode (Step 361 or the PCA mg mode (Step 362). If the care provider selects the PCA mL mode, the care provider is asked to enter the protocol of this mode, including the continuous rate (Steps 363 and 364), total volume (Steps 365 and 366), bolus volume (Steps 367 and 368), number of boli/hour (Steps 369 and 370), bolus interval (Steps 371 and 372), low volume alarm (Steps 373 and 374), protocol locking (Steps 375 and 376), and AIL on or off (Steps 377 and 378). If the care provider selects the PCA mg mode (Step 362), the care provider is asked to enter that mode's protocol, including the concentration (Steps 379 and 380), continuous rate (Steps 381 and 382), total volume (Steps 383 and 384), bolus volume (Steps 385 and 386), number of boli/hour (Steps 387 and 388), bolus interval (Steps 389 and 390), low volume alarm (Steps 391 and 392), protocol locking (Steps 393 and 394), and AIL on or off (Steps 395 and 396). After programming, the care provider is transferred (circle 397) to the sub-menus of FIG. 9.

Figure 9:
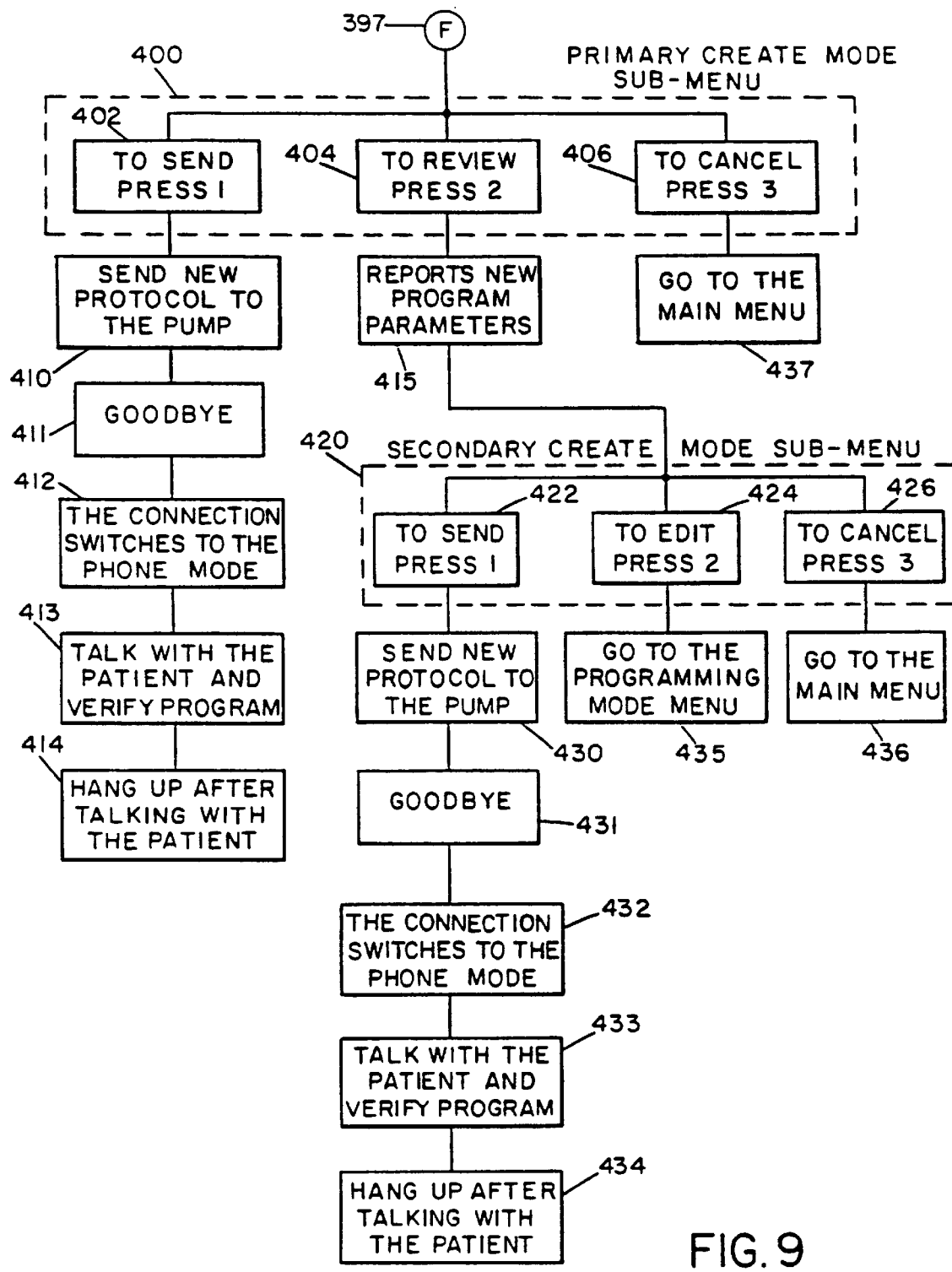
FIG. 9 is a flow diagram illustrating sub-menus of the programming mode menu in accordance with an example of the present invention.

Referring now to FIG. 9, after a programming sequence in accordance with FIGS. 8A, 8B and 8C, the care provider is transferred (via circle 397) to a primary create mode sub-menu 400. In the primary create mode sub-menu 400, the care provider can make various selections, including sending the newly programmed protocol (Step 402), reviewing the newly programmed protocol (Step 404), and cancelling the newly programmed protocol (Step 406). If the care provider selects send (Step 402), the care provider is told that the new protocol is being sent to the pump 12 and then told "goodbye" (Steps 410 and 411), and the connection is switched to the phone or patient conversation mode (i.e., communication with the patient) (Step 412). The care provider may then speak with the patient to verify the programming (Step 413) and then hang up after verifying (Step 414). If the cancel option 406 is selected, the care provider is transferred (Step 437) to the main menu 82.

If the review option 404 is selected, the parameters of the new programmed protocol are reported to the care provider (Step 415). The care provider is then transferred to a secondary create mode sub-menu 420, from which the care provider can select various options, including sending the new protocol (Step 422), editing the new protocol (Step 424), and cancelling the new protocol (Step 426). If the sending option 422 is selected, Steps 430 through 434 are performed, which are the same as those performed if the care provider were to select the sending option 402 from the primary create mode sub-menu 400. If the editing option 424 is selected, the care provider is transferred (Step 435) to the create mode menu 300. Finally, if the cancel option 424 is selected, the care provider is transferred (Step 436) to the main menu 82.

In all of the above processing modes, the homebase 14 can be provided with a variety of features that facilitates remote or local programming of the protocol. For example, "#" key can be used to enter changes or selections. The "*" key can be used for exiting the programming mode, for backspacing from a currently operating step to a previous step or from a portion of a parameter being processed to a previous portion of that parameter, or for entering a decimal point, depending on the instance in the programming sequence. The system can be set up such that it rejects out of range values and advises on the erroneous value. If the communicating phone line is equipped with call waiting, the existence of an incoming call on the additional call waiting line does not cause the presently communicating (i.e., programming) line to hang up.

Figure 10:
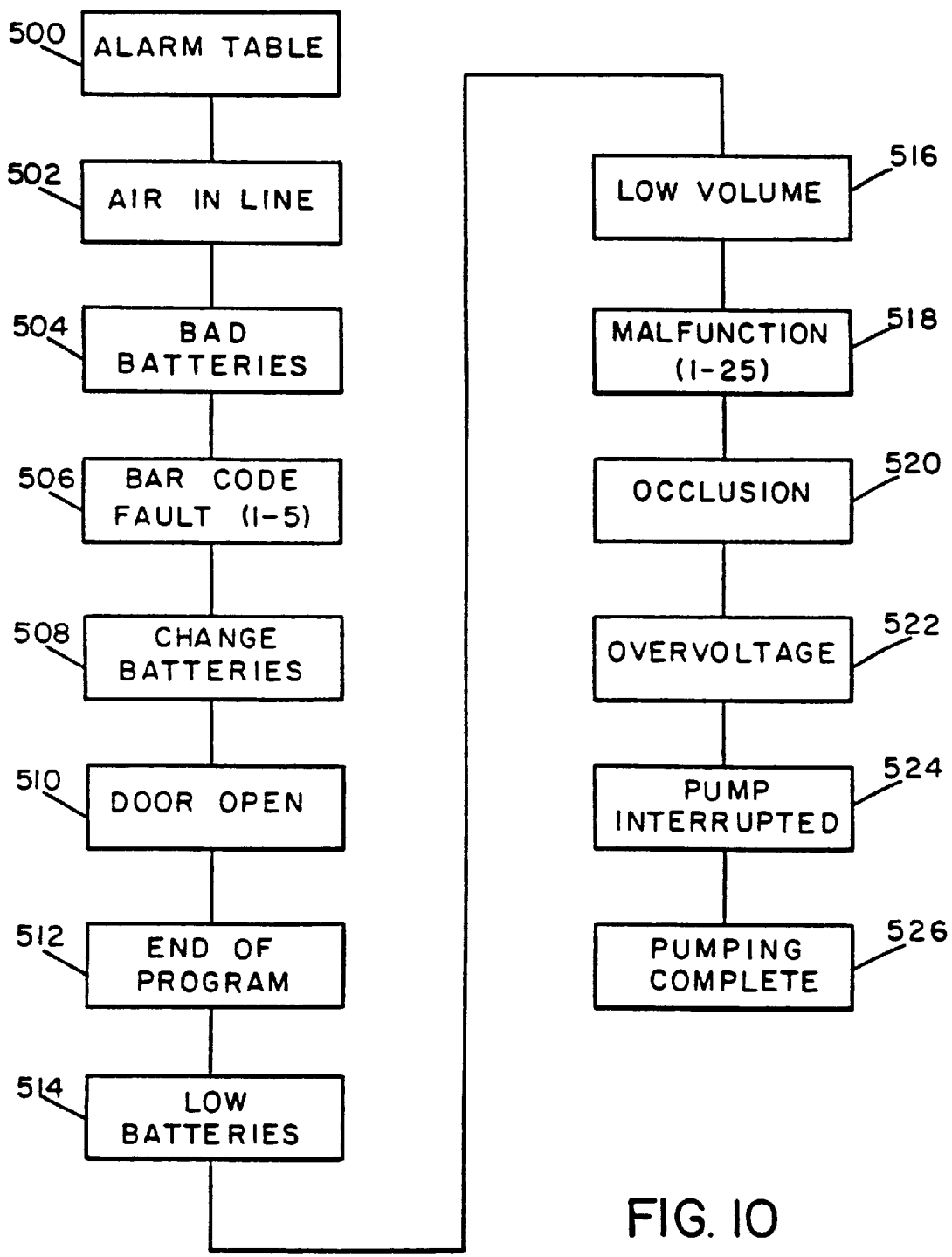
FIG. 10 is a table illustrating the alarm functions that can be employed in the system of the present invention.

With reference to FIG. 10, an alarm table 500 of the present invention will be described. The alarm table 500 may include a variety of alarm functions, including air in the line alarm 502 for the line 18 connecting the pump 12 to the patient, a bad battery alarm 504, a bar code fault alarm 506, an alarm indicating the need for a battery change 508, a door open alarm 510, an end of program alarm 512, a low battery alarm 514, a low volume alarm 516, a malfunction alarm 518, an occlusion alarm 520, an over-voltage alarm 522, a pump interrupted alarm 524, and a pumping complete alarm 526. All of these alarms can be made audible, with a variety of different or identical tones, or visual, via the alarm light 40, multiple lights, or a digital or analog display. The above alarm functions are exemplary, and other alarm functions can be provided. Alternatively, only some, or one, or none of the above alarm functions can be implemented in the present invention, depending on the particular application.

Examples of how the alarm light 40 and internal audio device 29 operate in response to various alarm conditions will now be described. The alarm light 40 may comprise a number of lights, for example, red, yellow, green, and other colored LEDs. The audio device 29 may comprise a speaker, siren, or similar apparatus. As an example of an alarm condition and the response thereto, if the phone line is improperly connected to the homebase unit 14 or the infusion system 10 is setup in some other improper manner, red and green LEDs (which comprise the alarm light 40) may flash together with intermittent audio from the audio device 29. If someone is trying to access the local mode (i.e., communicate with the homebase 14 via a local telephone connected to the local communication port 44) without the local telephone line being attached to the homebase 14, a yellow LED may flash with intermittent audio. If someone is trying to access the local, send, or link modes (i.e., is depressing the link button 30, local button 32, or send button 34) without the pump 12 being properly attached to the homebase 14, yellow and red LEDs may flash with intermittent audio. If the telephone connection between the remote or local telephone and the homebase 14 is lost, a red LED may flash with intermittent audio. Finally, if an internal system error occurs in the homebase 14 and/or pump 12, a red LED may flash with intermittent audio. It should be understood that the above operation of the alarm light 40 and audio device 29 are only exemplary and that variations can be made on these alarms.

It should also be understood that the above programming and functions described in FIGS. 3–10 provide only examples of how the care provider and the homebase unit 14 may interact via a remote or local push-button telephone or similar transceiver. Therefore, additional or alternative steps and procedures can be designed and implemented for remote programming of the present invention. Accordingly, only some of the steps described above need be included in the invention; the steps may be conducted in a different order; additional or fewer protocol parameters may be controlled by the care provider; and different operational modes (i.e., other than continuous, intermittent, etc.) may be chosen.

Furthermore, the present invention can be used in a variety of applications. In the exemplary application described herein, the present invention is used for controlling and programming the protocol of an infusion pump. A variety of infusion applications exist for which the present invention can be used, including ambulatory IVs, insulin pumps, hospital pumps, enteral pumps, blood pumps, intra-aortal pumps, subcutaneous pumps, and spinal (or epidural) pumps. Other medical applications also exist in which the present invention can be used for remote programming, as well as other functions described above, including use with ventilators (e.g., for blood/oxygen level), respiratory equipment, EKG machines, blood/gas analyzers, enteral pumps (i.e., stomach infusion pumps), blood glucose monitors, dialysis equipment, open wound irrigation devices, and urology equipment.

It will therefore be apparent to those skilled in the art that various modifications and variations can be made in the apparatus and method of the present invention without departing from the spirit or scope of the invention. Thus, it is intended that the present invention cover the modifications and variations of this invention, provided they come within the scope of the appended claims and their equivalents.

What is claimed is:

1. A remotely programmable infusion system having a programmable protocol, said remotely programmable infusion system being programmable by a remote touch-tone transceiver, comprising
    a memory for storing said programmable protocol;
    a voice storage unit for storing a voice signal;
    a remote communication port for sending said voice signal to said remote touch-tone transceiver and for receiving a remote programming signal from said remote touch-tone transceiver;
    an electronically controllable dispenser connectable in biomedical communication with a patient, for delivering medication to the patient; and
    a processor coupled to said remote communication port, said voice storage unit, said memory, and said dispenser, said processor configured to access said voice signal from said voice storage unit, said processor configured to access said programmable protocol in response to receiving said remote programming signal, said processor configured to control said dispenser;
    said infusion system configured to change a parameter of said biomedical communication in response to reprogramming of said protocol.

2. The remotely programmable infusion system recited in claim 1, wherein the remotely programmable infusion system has a user access code; wherein the processor permits remote programming of the programmable protocol in response to receiving said user access code from the remote touch-tone transceiver.

3. The remotely programmable infusion system recited in claim 1, wherein the remotely programmable infusion system has a user access code and a master access code; wherein the user access code is stored in the memory and is programmable; wherein the processor permits programming of the user access code in response to receiving said master access code from the remote touch-tone transceiver; and wherein the processor permits remote programming of the programmable protocol in response to receiving said user access code from the remote touch-tone transceiver.

4. The remotely programmable infusion system recited in claim 1, wherein the processor accesses a mode query signal from the voice storage unit, the remote communication port relays said mode query signal from the processor to the remote transceiver, and the processor selects one of a plurality of programming modes in response to a mode select signal being received from the remote touch-tone transceiver, said mode select signal being sent by the remote touch-tone transceiver in response to the remote touch-tone transceiver receiving said mode query signal.

5. The remotely programmable infusion system recited in claim 4, wherein the plurality of programming modes includes an edit mode for editing the programmable protocol, a review mode for reviewing the protocol, and a create mode for entering a new programmable protocol.

6. The remotely programmable infusion system recited in claim 1, further comprising a local communication port coupled to the processor, for relaying signals between the processor and a local touch-tone transceiver.

7. The remotely programmable infusion system recited in claim 1, wherein the remotely programmable infusion system has a status report mode, the remotely programmable infusion system further comprising a switch for selecting said status report mode; and wherein the processor accesses the programmable protocol from the memory in response to said status report mode being selected.

8. The remotely programmable infusion system recited in claim 7, wherein the remote communication port relays the programmable protocol from the processor to a computer in response to the processor accessing the programmable protocol.

9. The remotely programmable infusion system recited in claim 1, further comprising a programming access switch for selecting either a patient conversation mode or a programming mode, said programming mode providing programming of the programmable protocol by the remote touch-tone transceiver.

10. The remotely programmable infusion system recited in claim 9, further comprising an override circuit for bypassing the patient conversation mode and thereby directly initiating the programming mode.

11. The remotely programmable infusion system recited in claim 1, further comprising an alarm for indicating an alarm condition in the remotely programmable infusion system.

12. The remotely programmable infusion system recited in claim 1, wherein the voice signal is a digital voice signal, the system further comprising a voice synthesizer for converting said digital voice signal into an analog human voice signal, said analog human voice signal emulating the sound of a human voice.

13. A method for remotely programming an infusion system connectable in biomedical communication with a patient, said infusion system having a voice storage unit for storing a voice signal and having a programmable protocol, said infusion system being programmable by a remote touch-tone transceiver, the method comprising:
   establishing a connection between said infusion system and said remote touch-tone transceiver;
   accessing said voice signal from said voice storage unit after establishing said connection between said remote touch-tone transceiver and said infusion system;
   sending said voice signal to said remote touch-tone transceiver;
   receiving a remote programming signal from said remote touch-tone transceiver;
   programming said programmable protocol in response to receiving said remote programming signal; and
   said infusion system changing a parameter of said biomedical communication with said patient in response to changing of said programmable protocol.

14. The method recited in claim 13, wherein the infusion system has a user access code and the voice storage unit stores an access code voice command, the method further comprising;
   sending said access code voice command to the remote touch-tone transceiver in response to establishing the connection; and
   initiating a remote programming session for the programmable protocol in response to receiving said user access code from the remote touch-tone transceiver.

15. The method recited in claim 13, wherein the infusion system has a master access code and a user access code, wherein the user access code is programmable, and wherein the voice storage unit stores an access code voice command, the method further comprising:
   sending said access code voice command to the remote touch-tone transceiver in response to establishing the connection;
   initiating a remote programming session for said user access code in response to receiving said master access code from the remote touch-tone transceiver; and
   initiating a remote programming session for the programmable protocol in response to receiving said user access code from the remote touch-tone transceiver.

16. The method recited in claim 13, further comprising; accessing a mode query signal from the voice storage unit;
   sending said mode query signal to the remote touch-tone transceiver;
   sending a mode select signal from the remote touch-tone transceiver to the infusion system in response to said mode query signal; and
   selecting one of a plurality of programming modes in response to receiving said mode select signal.

17. The method recited in claim 16, wherein the plurality of programming modes includes an edit mode for editing the programmable protocol, a review mode for reviewing the programmable protocol, and a create mode for entering a new programmable protocol.

18. The method recited in claim 13, further comprising relaying signals between the infusion system and a local transceiver.

19. The method recited in claim 13, wherein the infusion system has a status report mode and a protocol memory for storing the programmable protocol, the method further comprising selecting said status report mode; and accessing the programmable protocol from the protocol memory in response to selecting said status report mode.

20. The method recited in claim 19, further comprising sending the programmable protocol to a computer in response to accessing the programmable protocol from the protocol memory.

21. The method in claim 13, further comprising selecting either a patient conversation mode or a programming mode, said programming mode providing for remote programming of the programmable protocol by the remote touch-tone transceiver.

22. The method recited in claim 21, further comprising bypassing the patient conversation mode and thereby directly initiating the programming mode.

23. The method recited in claim 13, further comprising detecting an alarm condition in the infusion system and indicating said alarm condition.

24. The method recited in claim 13, wherein the voice signal comprises a digital voice signal, the method further comprising converting said digital voice signal to a human voice signal, said human voice signal emulating the sound of a human voice.

25. A remotely programmable infusion system having a programmable protocol stored in a protocol memory, said remotely programmable infusion system being programmable by a remote touch-tone transceiver, comprising:
   an infusion pump for delivering fluids to a patient, said infusion pump having a pump data port; and
   a homebase unit, coupled to said pump data port on said infusion pump via a homebase data port, for processing said programmable protocol, said homebase unit comprising:
      a voice storage unit for storing a voice signal;
      a remote communication port for sending said voice signal to said remote touch-tone transceiver and for receiving a remote signal from said remote touch-tone transceiver; and
      a processor coupled to said remote communication port, said voice storage unit, and said protocol memory, for accessing said voice signal from said voice storage unit, for accessing said programmable protocol from said protocol memory, and for processing said programmable protocol to obtain a processed programmable protocol in response to said remote signal, said processed programmable protocol being relayed from said processor to said infusion pump via said homebase data port and said infusion data port.

26. The remotely programmable infusion system recited in claim 25, wherein the remote signal comprises a DTMF signal and wherein the remote touch-tone transceiver has a keypad, said keypad having a plurality of touch-tone keys, and the DTMF signal being generated by pressing one of said plurality of touch-tone keys.

27. The remotely programmable infusion system recited in claim 26, wherein the programmable protocol has a plurality of operating parameters, and wherein the voice signal comprises either a recorded voice command or a recorded voice query, said recorded voice command instructing a care provider operating the remote touch-tone transceiver to press at least one of the plurality of touch tone keys, and said recorded voice query asking said care provider operating the remote touch-tone transceiver to enter at least one of said plurality of operating parameters via the plurality of touch-tone keys.

28. The remotely programmable infusion system recited in claim 25, wherein the remotely programmable infusion system has a user access code; and wherein the processor permits remote programming of the programmable protocol in response to receiving said user access code from the remote touch-tone transceiver.

29. The remotely programmable infusion system recited in claim 25, wherein the remotely programmable infusion system has a user access code and a master access code; wherein the user access code is stored in an access code memory and is programmable; wherein the processor permits programming of the user access code in response to receiving said master access code from the remote touch-tone transceiver; and wherein the processor permits remote programming of the programmable protocol in response to receiving said user access code from the remote touch-tone transceiver.

30. The remotely programmable infusion system recited in claim 25, wherein the voice signal comprises a digital voice signal, the system further comprising a voice synthesizer for converting said digital voice signal to a human voice signal, said human voice signal emulating the sound of a human voice.

* * * * *

UNITED STATES PATENT AND TRADEMARK OFFICE
CERTIFICATE OF CORRECTION

PATENT NO. : 6,228,057 B1
DATED : May 8, 2001
INVENTOR(S) : Robert S. Vasko

It is certified that error appears in the above-identified patent and that said Letters Patent is hereby corrected as shown below:

Column 18,
Line 14, change "said protocol" to -- said programmable protocol --.
Line 44, change "the protocol" to -- the programmable protocol --.

Signed and Sealed this

Eighth Day of October, 2002

Attest:

JAMES E. ROGAN
Director of the United States Patent and Trademark Office

Attesting Officer